(12) United States Patent
Nagaraja et al.

(10) Patent No.: US 11,240,181 B1
(45) Date of Patent: Feb. 1, 2022

(54) ARTIFICIAL INTELLIGENCE ASSISTED SERVICE PROVISIONING AND MODIFICATION FOR DELIVERING MESSAGE-BASED SERVICES

(71) Applicant: Jiseki Health, Inc., San Mateo, CA (US)

(72) Inventors: Chandra Nagaraja, San Francisco, CA (US); Tushar Vasisht, San Mateo, CA (US)

(73) Assignee: Jiseki Health, Inc., Millbrae, CA (US)

( * ) Notice: Subject to any disclaimer, the term of this patent is extended or adjusted under 35 U.S.C. 154(b) by 0 days.

(21) Appl. No.: 17/093,596

(22) Filed: Nov. 9, 2020

Related U.S. Application Data

(63) Continuation of application No. 16/672,305, filed on Nov. 1, 2019, now Pat. No. 10,834,026.

(60) Provisional application No. 62/796,526, filed on Jan. 24, 2019.

(51) Int. Cl.

| | |
|---|---|
| *G06F 15/173* | (2006.01) |
| *H04L 12/58* | (2006.01) |
| *H04L 29/08* | (2006.01) |
| *G16H 80/00* | (2018.01) |
| *G06N 20/00* | (2019.01) |
| *G06N 5/02* | (2006.01) |
| *H04L 12/24* | (2006.01) |

(52) U.S. Cl.
CPC ............. *H04L 51/02* (2013.01); *G06N 5/027* (2013.01); *G06N 20/00* (2019.01); *G16H 80/00* (2018.01); *H04L 41/16* (2013.01); *H04L 67/16* (2013.01); *H04L 67/306* (2013.01)

(58) Field of Classification Search
CPC ......... H04L 51/02; H04L 67/16; H04L 41/16; H04L 67/306; G16H 80/00; G06N 5/027; G06N 20/00
See application file for complete search history.

(56) References Cited

U.S. PATENT DOCUMENTS

| | | | |
|---|---|---|---|
| 2015/0314454 A1* | 11/2015 | Breazeal ................ | B25J 9/0003 700/259 |
| 2018/0012137 A1* | 1/2018 | Wright ................... | G05B 15/02 |
| 2019/0268906 A1* | 8/2019 | Perdomo ........... | H04W 72/0453 |

* cited by examiner

*Primary Examiner* — Thanh T Nguyen
(74) *Attorney, Agent, or Firm* — Greenberg Traurig, LLP

(57) ABSTRACT

Systems and methods involving AI-assisted service provisioning and modification for delivering message-based services. One exemplary method includes: receiving an input sequence from a user in relation to a request for a service, the input sequence including one or more inputs; processing the input sequence to determine a service type; associating a workflow with the request based at least in part on the service type and a profile of the user, the workflow including a set of one or more steps, a step of the set of one or more steps corresponding to a set of attributes including at least one of: a communication mode, a communication type, or a communication priority, the workflow being performed by at least one of: a chatbot, an AI assistant, or a service professional; modifying the workflow based on a new input sequent from the user using a workflow engine comprising at least one of: an AI model, a machine learning model, and a ruleset; and interacting with the user based at least in part on the workflow to deliver the service.

23 Claims, 19 Drawing Sheets

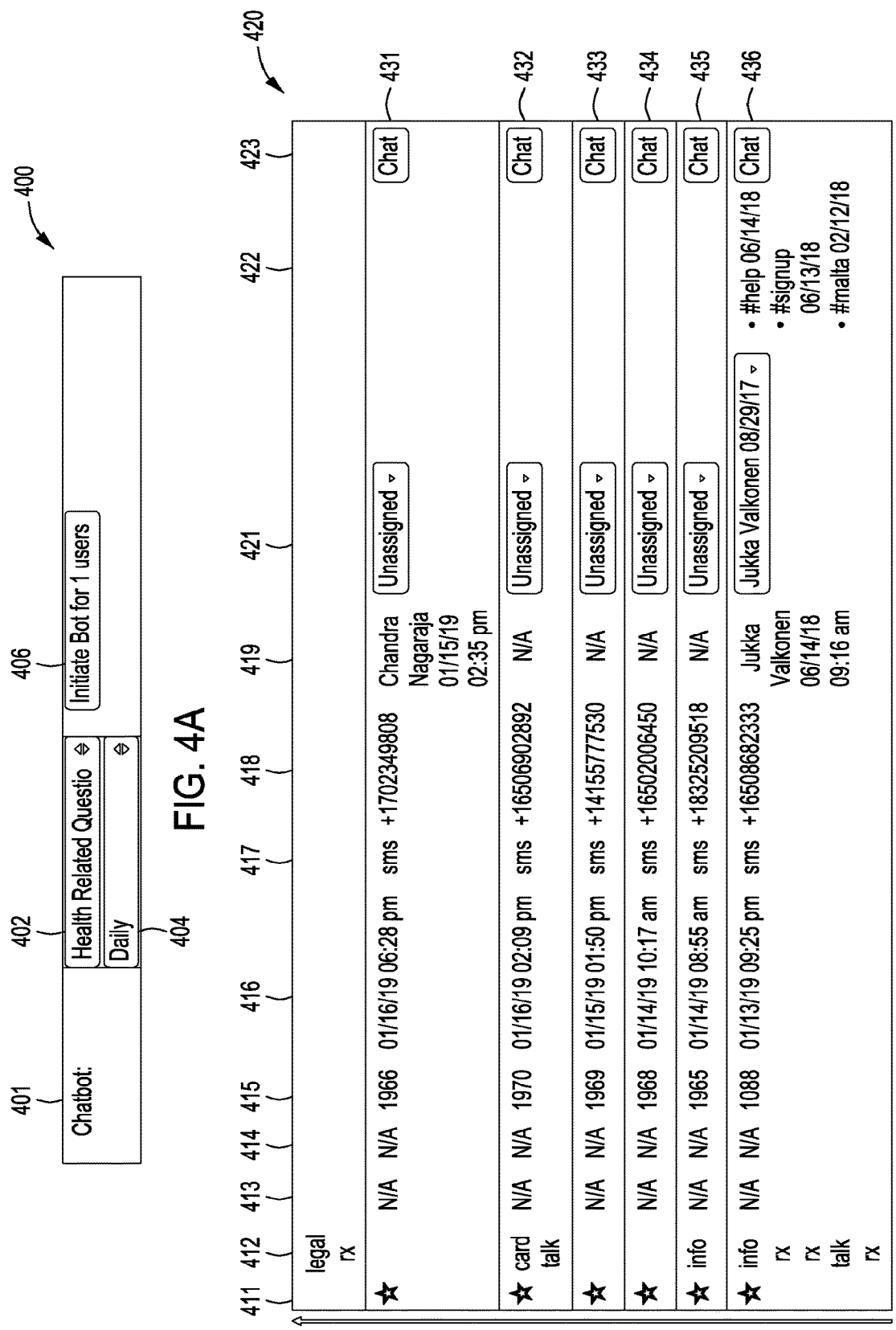

| JISEKI | CHATBOTS | ANALYTICS | CHATS | SETTINGS |

490-2 — 490-1

Agents

Flags and Roles
Notifications
Scheduling
Intergrations
HIPAA Hand-off
Company

Agent Table

490 ↙

490-3 — [Add Agent]

Search Agent          Show ▸

| | First Name | Last Name | Status | Role |
|---|---|---|---|---|
| ☐ | Justin | Schopick | Active | Admin |
| ☐ | Vagelis | Hristidis | Active | Admin |
| ☐ | Chandra | Nagaraja | Active | Admin |
| ☐ | Suraj | Vasanth | Active | Admin |
| ☐ | Jorge | Flores | Active | |
| ☐ | Alan | Barrett | Active | |
| ☐ | Jukka | Valkonen | Active | Medical - Rx |
| ☐ | Jukka | Valkonen | Active | Medical - Rx |

FIG. 4G

ARTIFICIAL INTELLIGENCE ASSISTED SERVICE PROVISIONING AND MODIFICATION FOR DELIVERING MESSAGE-BASED SERVICES

CROSS REFERENCE TO OTHER APPLICATIONS

The present application is a continuation of U.S. patent application Ser. No. 16/672,305, filed Nov. 1, 2019 and entitled "ARTIFICIAL INTELLIGENCE ASSISTED SERVICE PROVISIONING AND MODIFICATION FOR DELIVERING MESSAGE-BASED SERVICES," now U.S. Pat. No. 10,834,026, issued Nov. 10, 2020, which claims priority to U.S. Provisional Patent Application No. 62/796,526, filed Jan. 24, 2019 and entitled "ARTIFICIAL INTELLIGENCE ASSISTED SERVICE PROVISIONING AND MODIFICATION FOR DELIVERING MESSAGE-BASED SERVICES," the contents of all of which are incorporated by reference in entirety.

COPYRIGHT DISCLAIMER

A portion of the disclosure of this application contains material which is subject to copyright protection. The copyright owners has no objection to the facsimile reproduction by anyone of this application, as it appears in the Patent and Trademark Office patent file or records, but otherwise reserve all copyright rights whatsoever.

FIELD OF THE DISCLOSURE

The present invention relates generally to the field of computing technology, and more particularly, to artificial intelligence assisted service provisioning and modification for message-based services.

BACKGROUND

In our modern age, the availability and provision of adequate care services has not been satisfactory due to a variety of factors. Taking healthcare for example, medical advancement and innovation continues to focus on serving the insured population with high to medium income, instead of serving the general public in a more accessible and cost-effective manner.

Even with the deployment of telemedicine powered with low cost connectivity and ample computing resources provided by modern communication technologies, the prevalent issues remain to be the lack of sufficient number of doctors, the lack of knowledgeable and personalized consultations, as well as the lack of preventive programs such as awareness education and wellness care that are conveniently available.

Therefore, there exists a need for an effective, efficient, responsive, and self-evolving system for providing services to users in a personalized and holistic manner.

BRIEF OVERVIEW OF THE DISCLOSURE

The following presents a simplified summary of the disclosure in order to provide a basic understanding of some embodiments described herein. This summary is not an extensive overview, and it is not intended to identify key or critical elements to delineate the scope thereof. Some concepts are presented in a simplified form as a prelude to the more detailed description that is presented later.

Various embodiments are generally directed to methods of AI-assisted service provisioning and modification for delivering message-based services, executed by a processor coupled to a memory, for receiving an input sequence from a user in relation to a request for a service; processing the input sequence to determine a service type; associating a workflow with the request based at least in part on the service type and a profile of the user, the workflow including a set of one or more steps, a step of the set of one or more steps corresponding to a set of attributes including at least one of: a communication mode, a communication type, or a communication priority, the workflow being performed by at least one of: a chatbot, an AI assistant, or a service professional; and interacting with the user based at least in part on the workflow to deliver the service, comprising: receiving a new input sequence from the user; analyzing the new input sequence to determine a set of one or more elements, an element of the set of one or more elements triggering a change in the workflow; in response to the determination that the set of one or more elements is not empty, modifying the workflow based at least in part on the set of one or more elements; and responding to the request based on the workflow.

Various embodiments are further generally directed to systems for AI-assisted service provisioning and modification for delivering message-based services, the systems comprising a memory and a processor. The memory is configured to provide the processor with instructions which when executed cause the processor to: receive an input sequence from a user in relation to a request for a service; process the input sequence to determine a service type; associate a workflow with the request based at least in part on the service type and a profile of the user, the workflow including a set of one or more steps, a step of the set of one or more steps corresponding to a set of attributes including at least one of: a communication mode, a communication type, or a communication priority, the workflow being performed by at least one of: a chatbot, an AI assistant, or a service professional; and interact with the user based at least in part on the workflow to deliver the service, comprising to: receive a new input sequence from the user; analyze the new input sequence to determine a set of one or more elements, an element of the set of one or more elements triggering a change in the workflow; in response to the determination that the set one or more elements is not empty, modify the workflow based at least in part on the set of one or more elements; and respond to the request based on the workflow.

Various embodiments are also generally directed to computer program products comprising instructions for: receiving an input sequence from a user in relation to a request for a service; processing the input sequence to determine a service type; associating a workflow with the request based at least in part on the service type and a profile of the user, the workflow including a set of one or more steps, a step of the set of one or more steps corresponding to a set of attributes including at least one of: a communication mode, a communication type, or a communication priority, the workflow being performed by at least one of: a chatbot, an AI assistant, or a service professional; and interacting with the user based at least in part on the workflow to deliver the service, comprising: receiving a new input sequence from the user; analyzing the new input sequence to determine a set of one more elements, an element of the set of one or more elements triggering a change in the workflow; in response to the determination that the set of one or more elements is not empty, modifying the workflow based at least in part on the set of one or more elements; and responding to the request based on the workflow.

Various embodiments are disclosed in the following detailed description and the accompanying drawings.

BRIEF DESCRIPTION OF THE DRAWINGS

Various embodiments of the invention are disclosed in the following detailed description and the accompanying drawings.

The drawings described here are intended to further the understanding of the present invention, and form a part of the present application. The exemplary embodiment in the present application and its description are intended to explain the present invention, and do not constitute inappropriate limitation of the scope of the present invention. Among the drawings:

FIGS. 4A-G are graphic representations of example user interfaces of a portion of internal UI 214 of FIG. 2A, in accordance with one or more embodiments of the present disclosure;

DETAILED DESCRIPTION

Figure 1A:
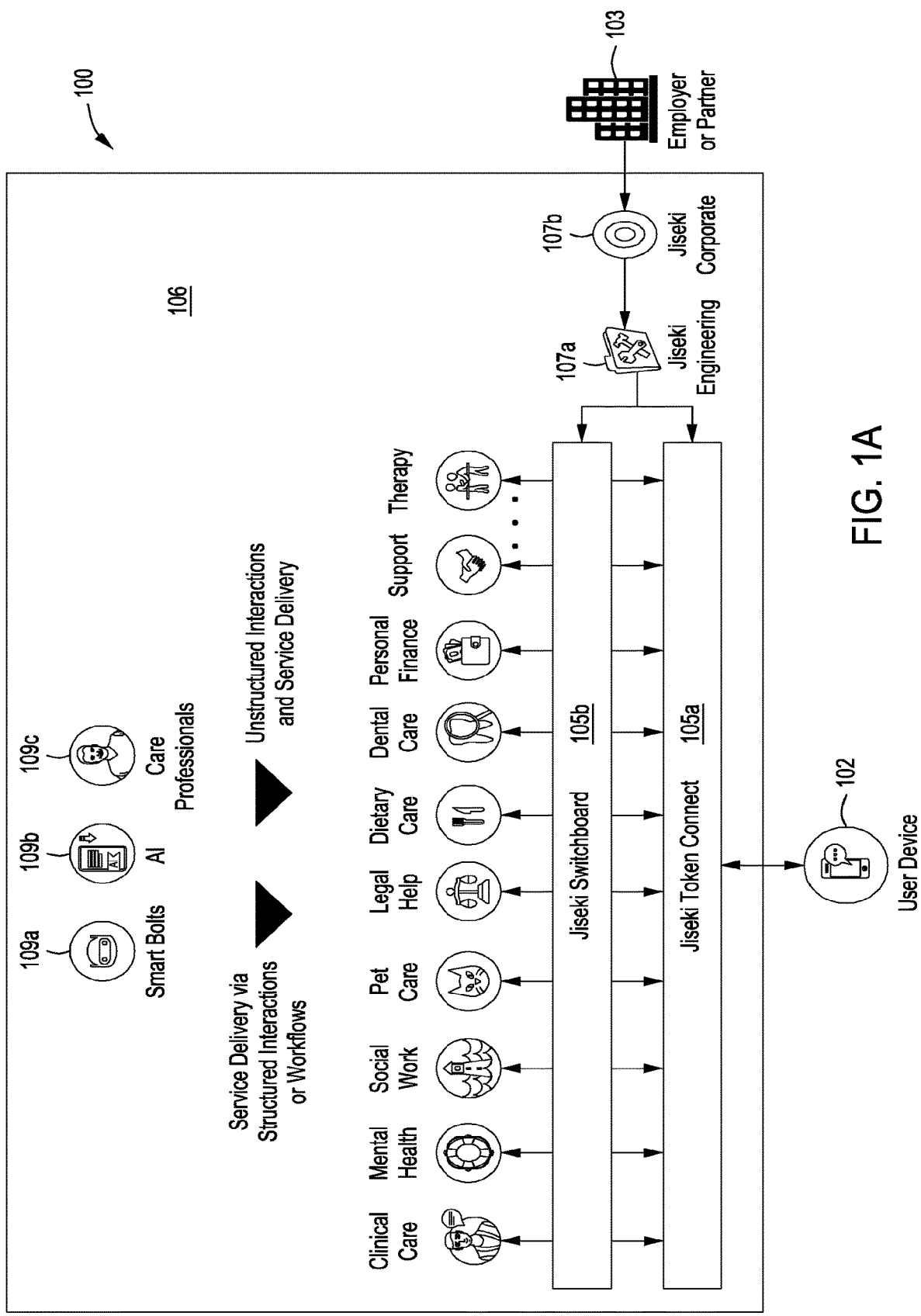
FIG. 1A is a simplified schematic diagram of an example system for AI assisted service provisioning and modification for delivering message-based services, in accordance with one or more embodiments of the present disclosure.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In order to allow persons skilled in the art to better understand the present invention, the technical solution of the present invention is described clearly and completely below in light of the drawings contained in the embodiments of the present invention. Obviously, the embodiments described are only a portion of the embodiments of the present invention, and do not represent the entirety of possible embodiments. Based on the embodiments contained in the present application, all other embodiments obtained from persons with ordinary technical skill in the art without the exertion of creative labor shall fall within the scope of protections of the present application.

It must be noted that the terms "first," "second," etc., in the description and claims of the present invention, as well as in the drawings, are used to differentiate similar objects, and are not necessarily intended to describe a specific order or sequence. It should be understood that data used in this way are interchangeable in the appropriate situations, so that the embodiments of the present invention described here can be implemented in sequences additional to those shown or described here. Moreover, the terms "comprises" and "has" and any variations thereof are intended to cover non-exclusive inclusion; for example, processes, methods, systems, products, and equipment that include a series of steps or units are not necessarily limited to the steps or units that are explicitly enumerated, but may comprise other steps or units that are not explicitly enumerated or are inherent to these processes, methods, systems, products or equipment.

Various techniques for providing AI-assisted service provisioning and modification for message-based service delivery are described herein. In various embodiments, a service platform receives a request for a service in user input, and processes the user input to provide the requested service to the user by identifying and associating a workflow with the request. Artificial intelligence models are used to provide assistance to updating a profile of the user, determining from the user input elements that trigger changes in the workflow, as well as modifying ruleset(s) used to generate the workflow. In some implementations, the user input includes a token that indicates a service type of the requested service, the token being pre-configured at the system. In some implementations, the token is customized according to a service need of the user. In some embodiments, the afore-described artificial intelligence models are created, trained, updated, and retrained using the communication between the user and/or other users, in relation to the delivering services of the same service type, and/or delivering services other than the service type, at the service platform.

Techniques described herein may give rise to various technical effects and advantages. For example, the more responsive, informative, helpful and efficient a message-based service system is providing services to its users, the more likely a user may be to communicate with the system in the future. The more a user communicates with a system, the more the system may be able to learn about the user and the knowledge in service domains. Consequently, the system is able to service its users in a more accurate, timely, personalized, and holistic manner, increasing the system's overall efficiency and conserving computing resources such as memory, power, processor cycles, and/or network bandwidth.

Furthermore, by segmenting interactions between a user and the system into a workflow of a plurality of steps associated with respective attributes, the system enables streamlining and automating steps common to providing services at a finer granularity. For example, a chatbot equipped with the correspondent knowledge (e.g., scripts to conduct domain-specific surveys or questionnaires, scripts personalized based on the service history) can always be provisioned as a first responder to incoming requests from users to minimize the waiting time from a user's perspective. At the same time, an automated step can nevertheless be taken over by a human professional, other chatbots or AI assistants, depending on, for example, changes or information newly detected or received at the system. Such design further facilitates a smoother, more effective, more efficient, and more agile collaboration between automation and professionals, automation and automation, as well as professionals and professionals. Empowered this way, the system allows, in a large scale, not only flexible service provisioning as well as modification, but also effective and efficient learning and training of automation.

Referring now to FIG. 1A, a schematic diagram of an example system for AI-assisted service provisioning and modification for delivering message-based services is illustrated in accordance with an embodiment of the present disclosure. System 100 depicts a platform 106 (e.g., Jiseki platform) in communication with a user (not shown) via a user device 102 as well as an affiliate entity (e.g., an employer or partner) 103. In some embodiments, platform 106 is configured to interface one or more chatbots 109a, one or more AI assistants 109b, as well as one or more professionals such as a care professional 109c (service providers other than care professional 109c not shown) for the purpose of delivering one or more services. In some embodiments, the one or more services provided by platform 106 includes, for example and without limitations, clinical care service, mental health services, pet care service, legal services, dietary care services, dental care services, financial services, support group services, group communication services, and therapy services.

In some embodiments, platform 106 includes a plurality of Jiseki token connects 105a (e.g., channels), through which the user at user device 102 (e.g., a desktop device, a mobile device, etc., and the details of which are described below with references to FIGS. 1B-C) can be connected via a communication network (e.g., wired network, wireless network, etc., network not shown and more details are described below with references to FIGS. 1B-C) by a Jiseki switchboard 105b into communication with one or more of the afore-described one or more services (e.g., clinical care, mental health care, financial, etc.).

In some embodiments, switchboard 105b identifies the user sending the incoming communication (e.g., messages, text, audio, video, data) using an identifier (e.g., a phone number, voice information, biometrical information, messaging app account, email account, social media account, IP address, or any combination thereof), and then accesses the profile of the user stored in system 100 (e.g., the services the user associated with the phone number is authorized to access, the context of any past/current/scheduled conversation(s) the user associated with the phone number is engaged in with platform 106, etc.). In some embodiments, switchboard 105b further accesses the profile of an employer/organization the user is associated with. In some embodiments, employer/organization profile information is included in the user profile information. Based on the profile information, it is determined whether to pass through the incoming communication to and thereby connecting the user to platform 106. Profile information will be described with more details with reference to FIGS. 2A-B.

In some embodiments, different tokens (e.g., keywords, hashtags such as #doc, #money, #talk, @talk, or equivalents in other languages (e.g., Spanish equivalents such as #medico, #dinero, and #hablar)) are set up at platform 106 to represent each respective service available at platform 106 (e.g., clinical care, mental health, etc. as shown in FIG. 1A). A token can be configured in a variety of forms. For example, a token can be designed as a word or an unspaced phrase prefixed with a designated identifier to form a label. A designated identifier includes, for example and without limitations, special characters or symbols such as the hash character (or pound sign), #; the "at" sign, @; the percentage sign, %; the dollar sign, $; the acclamation sign, !; the question mark, ?; the ampersand sign, &; the asterisk sign, *; and the like, as well as any combination thereof. A designated identifier can also include a word, a phrase, string of letters, string of words and/or phrases, string of any combination of letters, words/phrases, and special characters/symbols, or any combination thereof, as long as system 100 is configured with the knowledge that such identifier is meant as the prefix of a token. In some embodiments, a token can be designed as a word or an unspaced phrase post-fixed with the above-descried designated identifiers.

In some embodiments where incoming communication is not text based, e.g., incoming communication is an audio call, voice messaging, video messaging, emoji messaging, AR messaging, etc., a token is designed in appropriate forms to suit the nature of underlying communication mode. For example, with voice input, incoming communication is converted into text using various speech-to-text services (e.g., Google Cloud Speech) to transcribe the speech input into corresponding texts.

In an example where tokens are designed as hashtags, in some embodiments, one hashtag maps to one correspondent service available at platform 106. For example, #help designates a request for a service that gives the user a guide of the functions and services at platform 106; #doc designates a request for a medical or clinical service; #dentist designates a request for a dental service; #money designate a request for a financial service; #tax designates a request for a tax issue related service; #card designates a request for a credit card and/or debt card related service; #sara designates a request for a mental health chatbot service; #SOS designates a request to broadcast an emergency or urgent message to one or more communication groups pre-configured for the users at platform 106; #pet designates a request for a pet care related service; #dietitian designates a request for a dietary issue related service; and so on.

In some embodiments, one or more hashtags map to one correspondent service available at platform 106. For example, #doc and #consult can both designate a request for a clinical or medical service at platform 106. In some embodiments, hashtags are customized according to the needs and requests of users associated with a particular organization or users subscribing to a particular service. For example, for employees associated with a company A only, #allergy is recognized and mapped to a request for clinical care related to pollen-caused allergies according to the service provisioned for company A (located in a neighborhood having abnormal large population of flowering plants) at platform 106. However, when a user other than an employee of company A communicates #allergy to platform 106, the user is either not allowed access to the afore-described service associated with #allergy, or is only allowed to access a general allergy care, without the default assumption of the cause of the allergy. In some embodiments, one single hashtag maps to different levels of services available at platform 106. For example, depending on the level of services a user has signed up, or the user's organization has signed up on behalf of the user, #sara is mapped to a mental health service chatbot equipped with access to different knowledge bases or data stores corresponding to the respective subscription level. In some embodiments, hashtags are deleted when the usage of them become obsolete. In some embodiments, specially designed hashtags are time sensitive and only in effect through a designated period of time to address the needs for specific services during a period of time.

If the incoming communication (e.g., an input sequence) includes a recognized token, such as a hashtag, it is compared against the user's access permissions (e.g., whether the user can access the service activated by the token) as a further filter. Once the user's message is sent through, the interaction may be automated, manual, or a combination thereof, as determined by the pre-determined protocols/algorithms/rulesets/AI and the workflows the user is in the midst of. In some embodiments, each service channel has its own workflows and messages that flow back to the user, sometimes unprompted.

In some embodiments, authorized users at user device 102 use those tokens, which involves/entails sending platform 106 messages that contain the tokens, to connected to corresponding services. Certain selected services may only be accessible to certain users based on information such as organizational affinity (e.g., employees of a certain company purchasing a portion of service access to platform 106 can only talk to Jiseki's financial advisor, or a patient referred by a mental health professional can only interact with service available through #talk), profile, or payment/membership status, etc. Unknown users may be able to use certain tokens to access specific services at no cost, and many other users can be pre-imported into the system to be recognized when they message platform 106.

In some embodiments, platform 106 includes one or more smart bots 109*a*, one or more AI and/or machine learning enabled assistants 109*b* in addition to interfacing one or more professionals such as a care professional 109*c*. The smart bots 109*a*, AI assistants 109*b*, and the professionals (e.g., service providers such as a nurse, doctor, lawyer, CPA, therapist, physiatrist, social worker, etc.) participate in providing the afore-mentioned one or more services to the user. In some embodiments, the afore-described professionals include their own smart bots (not shown), AI assistants (not shown), or any form of machine learning entities (not shown). In some embodiments, smart bot 109*a* (e.g., chatbot) is implemented using a combination of one or more rules, and/or keyword analysis. For example, a chatbot can be designed to mimic human conversation. In some embodiments, AI assistant 109*b* is implemented using artificial intelligence and/or any form of machine learning, and/or AI algorithms. In some embodiments, smart bot 109*a* is tasked to provide chat services to the user in a style of scripted or rule-based conversation (e.g., structured conversation). In some embodiments, AI assistant 109*b* is tasked to provide chat services to the user in a style of open ended, free flowing conversation (e.g., unstructured conversation). In some embodiments, structured conversation types refer to defined interactions (e.g., surveys) or a particular pre-crafted message defined in the workflow rulesets. In some embodiments, an unstructured conversation, or freeform conversation, results from either platform 106 or the user deciding to engage in an undefined (e.g., discovery) process. This could mean conversation with a professional, but it may also mean conversation with AI assistant 109*b* capable of natural language processing. Based on the results of either one or both, it is determined whether a new workflow is to be generated, or an existing workflow is to be customized. As described with more details below with references to FIGS. 4A-G, in some embodiments, an operational dashboard (e.g., a professional console UI, internal UI, control UI) is configured to enable the professional to perform either or both of these afore-described tasks (e.g., generating a new workflow, modifying an existing workflow) manually. In some embodiments, such tasks are performed automatically after and/or assisted by analyzing the conversation pattern, and/or information collected during the service delivery. In some embodiments, a workflow is initiated according to a structured conversation and performed by smart bot 109*a* (e.g., a rule-based bot, chatbot). In some embodiments, chatbots and AI assistants both refer to any form of conversation automations.

In some embodiments, platform 106 is configured to include various administrative components 107, which are used, among other things, to provide platform 106 with various functionalities and/or data required in order to undertake the delivering of the one or more services to the user. For example and as illustrated herein, administrative components 107 include Jiseki engineering 107*a* and Jiseki corporate 175*b*. Jiseki engineering 107*a* is configured to enable entities such as Jiseki administration and/or engineering personnel to undertake various functions pertaining to, for example and without limitations, the setup of platform 106, provisioning and configuration of platform 106, and maintenance and modification of platform 106. In some embodiments, Jiseki engineering 107a enables Jiseki administrative/engineering personnel to implement rulesets that dictate, for example and without limitations, how to associate a user with a service (e.g., a workflow of a service) based on various conditions, how to modify a workflow based on user input information, the profile data, chatting history data on the particular channel associated with the service and/or the user, chatting history data on channels other than the particular channel associated with the service and/or the user, and so on. Furthermore, Jiseki engineering 107a enables Jiseki administrative/engineering personnel to implement tokens and their mapping relationship with corresponding services, set up individuals and/or organizations whose members/affiliates/agents for access/subscription to groups of particular one or more services provided at platform 106, and register professionals (e.g., agent) with authorized role-based access to platform 106 to service users.

In some embodiments, Jiseki engineering 107a enables the access to third party tools (e.g., payment services, calendar appointment service, medication prescription service, etc.), in connection with delivering the afore-described one or more services to the user. More details are described below with reference to FIGS. 2A-B.

In some embodiments, Jiseki corporate 107b is configured to create, manage, and maintain, for example and without limitations, user profiles, organization/employer profiles, subscription rules, access rules, privacy policies, one or more databases mapping tokens designating various channels corresponding to various services, etc. In some embodiments, Jiseki corporate 107b interfaces with one or more affiliate entities such as employer/partner 103 to provide and/or customize services to the employee/agents associated with employer/partner 103. In some embodiments, Jiseki corporate 107b also interfaces with individual users to provide/customize services delivered through platform 106.

In some embodiments, Jiseki cooperate 107b engages directly with users/parties for delivering services through, for example and without limitation, advertisement and/or direct recruitment. On the other hand, Jiseki corporate 107b also engages employer/partner 103 (e.g., third party employers, organizations, government partners, etc.) to sign up users with services (e.g., pre-authorized services, pre-paid services, etc.) in association with service channel designating tokens (e.g., generic Jiseki token, customized token, time-sensitive token, etc.). Although only one user device 102, one Jiseki platform 106, one smart bot 109a, one AI assistant 109b, one care professional 109c, one Jiseki engineering 107a, one Jiseki corporate 107b, one employer/partner 103, and a limited number of services and their correspondent channels are shown in FIG. 1A, system 100 can include any number of user devices 102, Jiseki platforms 106, employer/partner 103, as well as services and professionals; and Jiseki platform 106 can include any number of smart bots 109a, AI assistants 109b, care professionals 109c, as well as services in other embodiments.

Figure 1B:
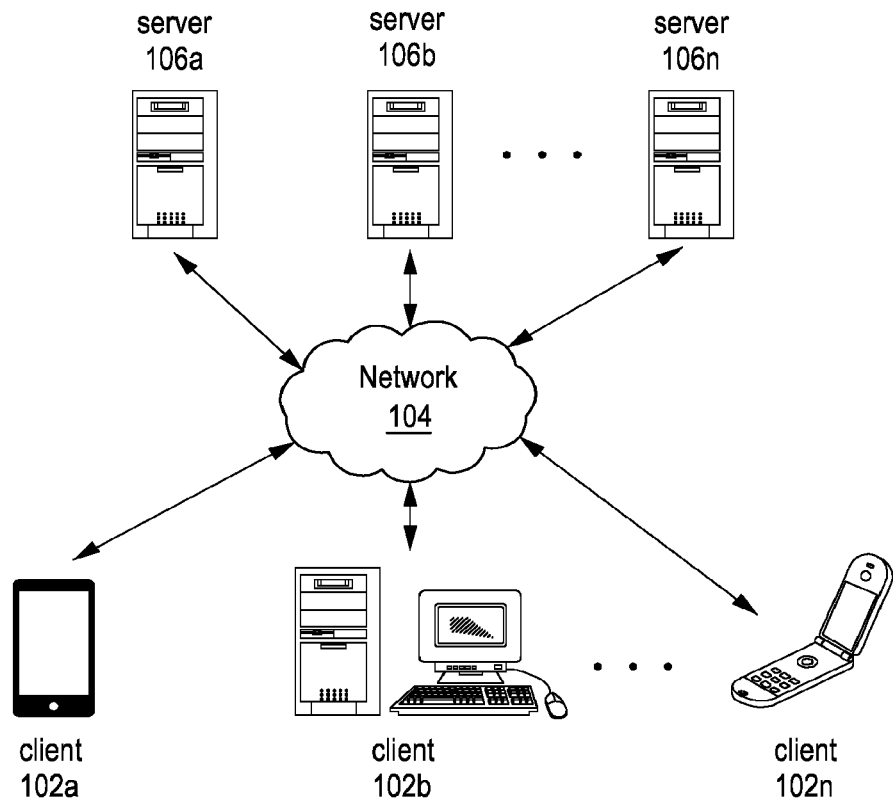
FIG. 1B is a block diagram of an example network computing environment for AI assisted service provisioning and modification for delivering message-based services, in accordance with one or more embodiments of the present disclosure.

FIG. 1B illustrates an example network computing environment for AI assisted service provisioning and modification for delivering message-based services in accordance with an embodiment of the present disclosure. The network computing environment includes one or more clients 102a-102n (also generally referred to as client(s) 102, client device(s) 102, user device(s) 102, and end device(s) 102) in communication with one or more servers 106a-106n (also generally referred to as server(s) 106) via one or more networks 104.

In some embodiments, clients 102 and servers 106 are configured on the same network 104. In some other embodiments, clients 102 and servers 106 are in communication via multiple networks 104 configured therebetween. In some embodiments, network 104 is a private network, a public network, or a combination thereof. In some embodiments, network 104 includes one or more networks such as a data network, a wireless network, a telephony network, or any combination thereof. It is further understood that the data network can be any body area network (BAN), personal area network (PAN), local area network (LAN), metropolitan area network (MAN), wide area network (WAN), public data network (e.g., the Internet), and the like. The wireless network can be, for example, a cellular network employing various technologies such as general packet radio service (GPRS), global system for mobile communications (GSM), Enhanced Data GSM Environment (EDGE), Internet protocol multimedia subsystem (IMS), universal mobile telecommunications system (UMTS), or the like; as well as any other suitable wireless medium, e.g., worldwide interoperability for microwave access (WiMAX), code division multiple access (CDMA), wideband code division multiple access (WCDMA), wireless fidelity (Wi-Fi), wireless LAN (WLAN), Bluetooth®, Bluetooth Low Energy (BLE), ANT/ANT+, Z-Wave, ZigBee, NFC, infrared channel, and the like, or any combination thereof. Network 104 can be an overlay network that is a virtual network enabled on top of one or more layers of other network 104. Network 104 can also be any such network, known to those ordinarily skilled in the art, that are capable of supporting the operations described herein. Network 104 can be implemented using various techniques and layers or protocol stacks including, for example and without limitations, Ethernet protocol, the internet protocol suit (TCP/IP), the ATM (Asynchronous Transfer Mode) suit, the SONET (Synchronous Optical Networking) protocol, the SDH (Synchronous Digital Hierarchy) protocol, and the like.

In some embodiments, server 106 may include a group of servers 106 (e.g., multiple logically-grouped servers 106, server farm(s) 106). In some embodiments, servers 106 may be geographically dispersed. Servers 106 within a server farm can include both heterogeneous servers and homogenous servers. In other words, one or more servers 106 within a server farm can operate according to one type of operating system (e.g., Windows), while one or more of the other servers 106 can operate according to other types of operating systems (e.g., Linux, Unix, Mac OS).

In some embodiments, servers 106 in a server farm may be implemented at high-density rack systems with associated storage system, and located in a consolidated space (e.g., a data center, an enterprise center). In this way, various techniques can be implemented to improve system performance, data security, physical security, and system manageability. In some embodiments, servers 106 within a server farm may not be physically proximate to another server 106 within the same server farm. The logically-grouped servers 106 as a server farm can be interconnected using a wide-area network (WAN) connection, a metro-area network (MAN) connection, or the like. For example, a server farm can include servers 106 physically located in different continents, regions of the continents, countries, states, cities, data centers, etc. The logically-grouped server 106 as a server farm can also be interconnected using local-area network (LAN) connection or other forms of direct connection with increase speeds of data transmission.

Server 106 may be a messaging server, file server, application server, web server, proxy server, appliance, network appliance, gateway, gateway server, virtualization server, deployment server, SSL VPN server, firewall, or the like. In some embodiments, a plurality of servers 106 may be in the path between any two communicating servers 106.

Client devices 102 can be any type of computing device (e.g., a device with a processor and memory) such as a mobile terminal, fixed terminal, or portable terminal. For example, client devices 106 can include a mobile phone, a smart phone, a smart watch, a tablet, a desktop computer, a laptop computer, a Personal Digital Assistants (PDAs), a media playing device, a gaming system, an in-vehicle device, an IoT device, a wearable device, a server, and the like. Client devices 106 are equipped with sufficient processing power and memory capacity to perform the operations described herein. In some embodiments, client device 102 can include different operating systems, processors and input/output components configured for the device. In some embodiments, client device 102 may include a combination of devices, e.g., a smart phone combined with a wearable smart fitness device. In some embodiments, client devices 102 may function as both a node in communication with a server and as a server providing access to hosted resources for other clients 102.

Figure 1C:
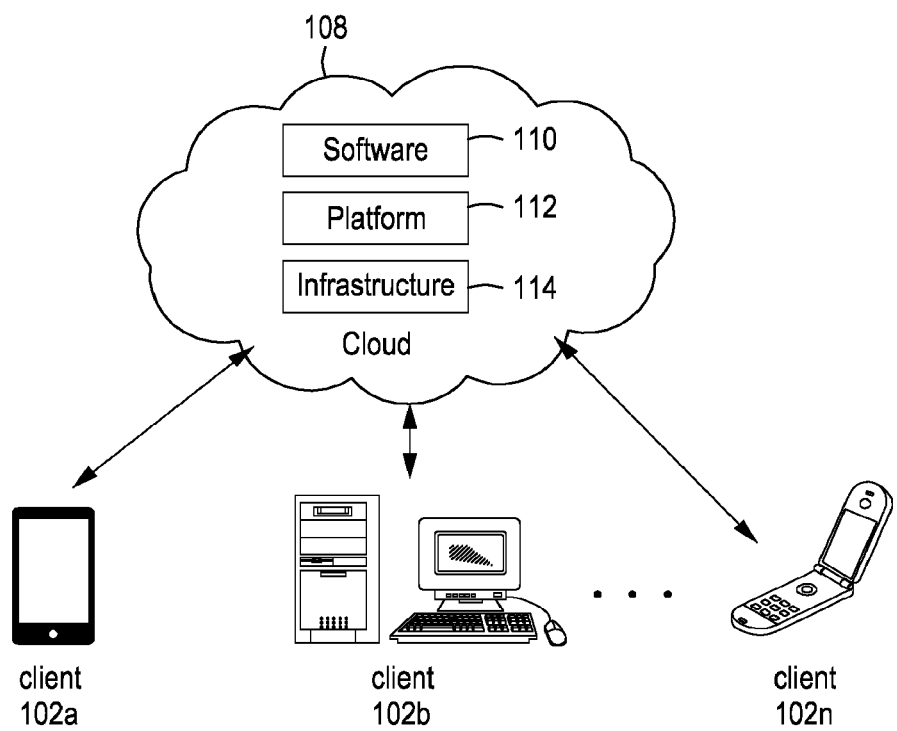
FIG. 1C is a block diagram of an example cloud computing environment for AI assisted service provisioning and modification for delivering message-based services, in accordance with one or more embodiments of the present disclosure.

FIG. 1C illustrates an example cloud computing environment for AI assisted service provisioning and modification for delivering message-based services in accordance with an embodiment of the present disclosure. A could computing environment is configured to provide clients 102 with resources provided by the afore-described network computing environment. The cloud computing environment includes one or more clients 102a-102n in communication with cloud 108 via one or more networks 104. Client 102 may include, for example and without limitations, a zero client, thin client, as well as zero client. As used herein, both a thin client and a zero client refer to a client that may depend on cloud 108 and/or server 106 in order to provide some of its functionality. A zero client may further depend on cloud 108 and/or server 106 in order to retrieve operating system data for client 102. A thick client may be configured to provide some functionality when disconnected from cloud 108 or server 106. Cloud 108 may be public, private, or a combination thereof (e.g., hybrid). Public cloud may be connected to servers 106 over one or more public networks; while private cloud may be connected to private servers 106 via one or more private networks. In some embodiments, private cloud can include private servers that are maintained by clients 102 or owners of clients 102. Hybrid cloud may include both private and public servers, as well as both private and public networks.

Cloud 108 can include a cloud based services, for example and without limitations, Software as a Service (SaaS) 110, Platform as a Service (PaaS) 112, and Infrastructure as a Service (IaaS) 114. As used herein, IaaS refers to online services that deliver various underlying computing functionality such as storage, networking, server, security, virtualization, backup, and the like. In some embodiments, IaaS allows a user to access (e.g., rent) the afore-described computing infrastructure that are needed during a specific period of time period in order to scale up quickly. Examples of IaaS includes Google Compute Engine provided by Google Inc., Rackspace Cloud provided by Rackspace Inc., and Amazon Web Services (AWS) provided by Amazon Inc. PaaS offers, in addition to those computing functionalities provided by IaaS, computing resources including, for example and without limitations, the operating system, middleware, database, or runtime resources. Examples of PaaS include Windows Azure provided by Microsoft Corp., Google App Engine provided by Google, Inc., and Oracle Cloud provided by Oracle Corp. SaaS providers offer additional resources such as application and data resources. Examples of SaaS include Google Apps provided by Google Inc., Office365 provided by Microsoft Corp., Dropbox provided by Dropbox Inc., iCloud provided by Apple Inc.

Client 102 may access IaaS services using one or more IaaS standards including, for example and without limitations, Open Cloud Computing Interface (OCCI), Cloud Infrastructure Management Interface (CIMI), Amazon Elastic Compute Cloud (EC2), and OpenStack standards. Client 102 may access PaaS services using one or more PaaS interfaces including, for example and without limitations, HTTP, Java APIs, JavaMail API, Java Data Objects (JDO), Java Persistence API (JPA), Python APIs, web integration APIs such as Rack for Ruby, WSGI for Python, and PSGI for Perl, and the like. Client 102 may access SaaS resources through web-based user interfaces provided by, for example and without limitations, a web browser (e.g., Google Chrome, Mozilla Firefox, Microsoft Internet Explorer). Client 102 may also access SaaS resources via applications on smartphones, tablet or smart devices; as well as through the operating system of client 102.

Figure 2A:
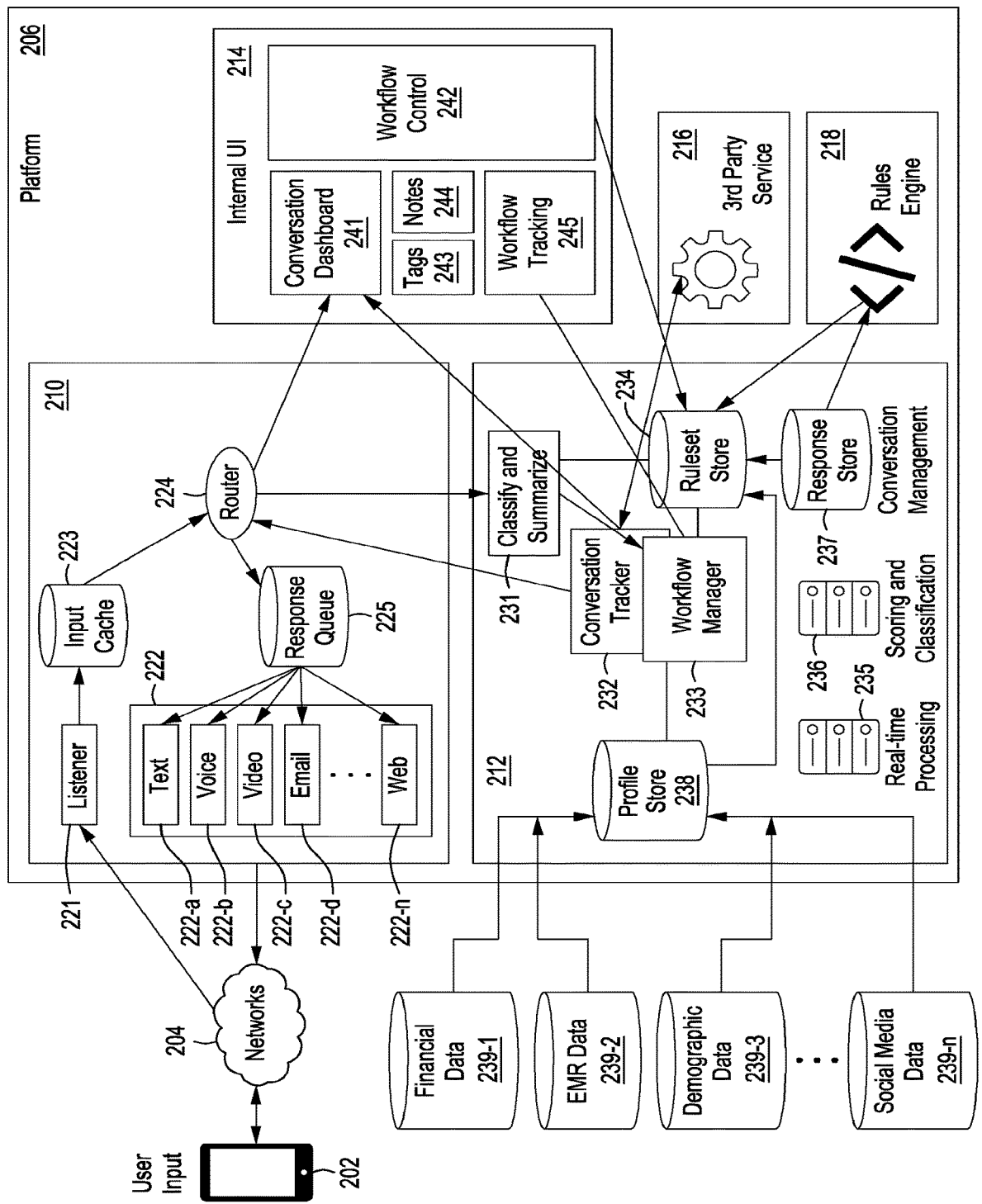
FIG. 2A is a simplified block diagram of some of the architecture of a system for AI assisted service provisioning and modification for delivering message-based services, in accordance with one or more embodiments of the present disclosure.

FIG. 2A illustrates an example block diagram of some of the architecture of a system for AI assisted service provisioning and modification for delivering message-based service in accordance with an embodiment of the present disclosure. System 200 includes a client 202 in communication with a platform 206 via a network 204. At client 202, a user (not shown) sends an input sequence over network 204 to platform 206 in order to request a service and/or receive and engage in communication with platform 206. In some embodiments, client 202 can be implemented by, for example and without limitations, client 102 of FIGS. 1A-C; and network 204 can be implemented by, for example and without limitations, network 104 of FIGS. 1A-C. Platform 206 can be a part of one or more servers 106. In some embodiments, tasks performed by platform 206 can be performed by a plurality of servers 106, e.g., being allocated amongst the plurality of servers by an application, service, process, daemon, routine, executable logic, or other task allocation techniques. In some embodiments, platform 206 can be implemented at, for example and without limitations, servers 106 of FIGS. 1A-B, and/or cloud 108 of FIG. 1C.

In some embodiments, platform 206 includes a message execution module 210, a conversation management module 212, a rule engine 218, an Internal UI module 214, and a set of one or more third party services 216. In some embodiments, it should be appreciated that the set of one or more third party services 216 can also operate independently from platform 206.

Each of platform 206, message execution module 210, conversation management module 212, internal UI module 214, rule engine 218, set of one or more third party services 216, and any components or sub-modules thereof, can be embodied as hardware, software, firmware, or a combination thereof. Such software can include, for example and without limitations, a program, service, task, script, library, application, service, or any form of executable instructions on one or more processors. Any of these afore-described modules, components, and sub-modules may be combined into one or more modules, components, sub-modules, applications, programs, services, tasks, scripts, libraries, or executable code.

Figure 8:
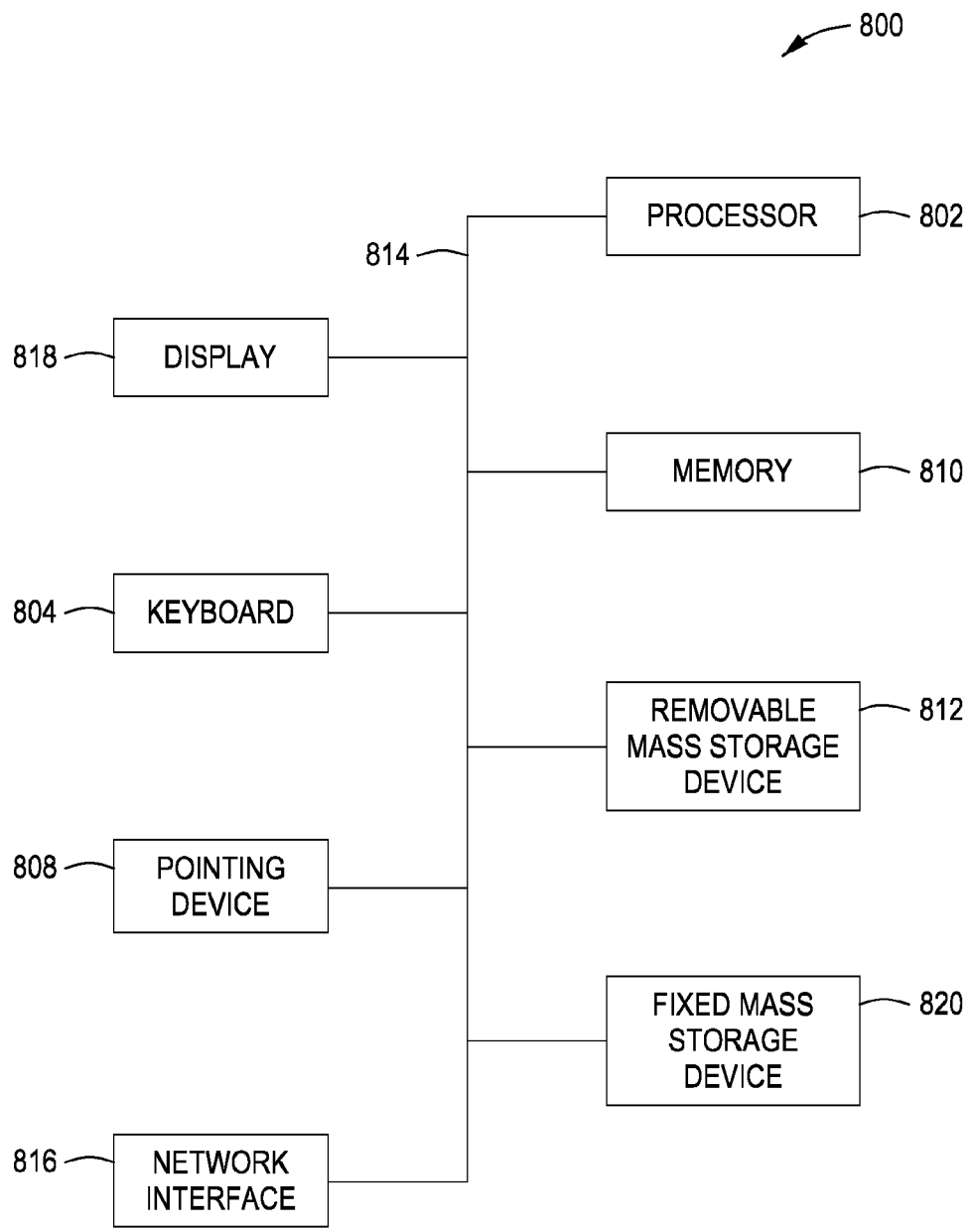
FIG. 8 is a simplified functional diagram of an embodiment of a programmed computer system for AI assisted service provisioning and modification for delivering message-based services, in accordance with one or more embodiments of the present disclosure.

For example, the various modules, components, sub-modules, and logic of platform 206 can form a portion of, or otherwise be established by, the processor 802 of FIG. 8 or other computing device.

In some embodiments, message execution module 210 includes a listener 221, a communication module 222, an input cache 223, a router 224, and a response queue 225. In some embodiments, along an inbound path, listener 221 is configured to receive inputs incoming from the user to platform 206, and in turn forward the received inputs from the user to input cache 223 for forwarding to router 224, which eventually further forwards the received inputs to conversation management module 212 for processing. Along an outbound path, router 224 is configured to receive one or more responses in relation to the inputs from conservation management module 212, and store the received one or more responses in response queue 225, which in turn forwards the one or more responses to communicate module 222 including worker such as text worker 222-a, voice worker 222-b, video worker 222-c, email worker 222-d, and web worker 222-n, etc. Communication module 222 is configured to eventually transmit the one or more responses to the user as a result of receiving the inputs from the user according to the appropriate communication mode enabled by its workers.

In some embodiments, listener 221 can be configured as a portal in receipt of SMS or MMS based incoming communication addressed to a short code. In some embodiments, a short code is a sequence of five or six digits of phone number, or a sequence of any digits of phone number, associated with platform 206. In some embodiments, listener 221 can be configured with one or more short codes that are associated with platform 206. For another example, listener 221 can be configured as a portal in receipt of messages addressed to one or more accounts of a messaging application (e.g., Facebook Messenger®, SnapChat®, Slack®, iMessage®, KaoKaoTalk®, DingTalk®, Skype®, WhatsApp®, Line®, WeChat®, Telegram®, Discord®, Instagram®, Google Hangouts®, Twitter®, avatar messaging, virtual reality application, gaming application, and the like) that are associated with platform 206. In some other examples, listener 211 can be configured to receive inputs from the user in formats other than text such as email, voice, video, etc.

In some embodiments, router 224 is configured to process the input sequence and determine whether the received input sequence includes any tokens (e.g., hashtags) recognizable at platform 206, and accessible to the particular requesting user. In some embodiments, router 224 is further configured to retrieve the profile information associated with the requesting user from a profile store 238 to identity the detailed service level provisioned for the particular user corresponding to the received token(s). This way, a service type is determined from the incoming input sequence. In some embodiments, router 224 is configured to also forward a copy of the input sequence to internal UI 214 for displaying. For example, incoming input sequence can be displayed via a conversion dashboard 241 of internal UI 214.

In some embodiments and as illustrated herein, communication module 222 includes one or more of a text worker 222-a, a voice worker 222-b, a video worker 222-c, an email worker 222-d, and a web worker 222-n. Via text worker 222-a, platform 206 is configured to generate and communicate text messages with the user in any appropriate manner. Via voice worker 222-b, platform 206 is configured to generate and communicate voice messages with the user in any appropriate manner. Via video worker 222-c, platform 206 is configured to generate and communicate video messages and/or sessions with the user in any appropriate manner. Via email worker 222-d, platform 206 is configured to generate and communicate email messages with the user in any appropriate manner. Via web channel 222-n, platform 206 is configured to generate and communicate landing web pages and/or sessions with the user in any appropriate manner.

In some embodiments, communication modes to be executed by communication module 222 are determined based on the response(s) fetched from response queue 225 for transmission to the user. In some embodiments, responses generated from conversation management module 212 are stored in response queue 225 and configured with an indicator that designates in which manner the responses are to be communicated to the user. In some embodiments, the indicator is determined based on the communication mode information specified by the steps of a workflow that is identified and associated with the users in response to the inputs therefrom and/or the processed inputs. For example, when the user's input to platform 206 triggers a response from a care professional (e.g., a doctor) that has to be communicated in compliance with patient privacy standards set forth in regulations such as, for example and without limitations, the Health Insurance Portability and Accountability Act (HIPAA), a HIPAA compliant video link is included in a text message for transmission to the user as part of the response. Upon clicking on the video link embedded in the message, the user traverses to a HIPAA-enabled landing web page in a web browser to consult with the care professional, with the ease of mind that none of the user's privacy information such as medical records or data are exchanged or accessed beyond the bounds of governing laws, regulations, and/or guidelines. Using the same context of the user consulting with a care professional on medical matters, at a certain point of the HIPAA-enabled communication, the care professional might decide to ask a nurse to send the user some self-educational medical materials so that the user can become more knowledgeable of certain medical matters. As text messages are usually limited in the number of words, an email link can be embedded in a text message to be transmitted to the user, and an email can also be generated and sent to the user at an email account known to platform 206.

In some embodiments, platform 206 is configured to generate a set of one or more responses in receipt of an input from the user. In some embodiments, each response of the set of one or more responses bears the same type of communication mode indicator such that each response is to be transmitted to the user via the same communication mode by communication module 222. For example, all the responses of a set of one or more responses can be sent to the user via SMS. In some other embodiments, one or more responses of the set of one or more responses can have a communication mode indicator different than the other one or more responses of the set of one or more responses. For example, in reply to an input from the user, a first response of a set of responses is to be transmitted via SMS, a second response of the set of responses is to be transmitted via an audio link, and a second response of the set of response is to be transmitted via SMS again. In some embodiments, the multiple communication modes associated with a set of one or more responses are determined based on the communication modes of the one or more steps associated with a workflow identified and assigned to addressing the inputs of the user. In some embodiments, the communication mode associated with a particular step is a fixed mode. In some other embodiments, the communication mode associated with a particular step can be modified based on the information/content exchanged between platform 206 and the user, platform 206's knowledge or any types of intelligence of the user, or groups of users.

In some embodiments, text worker 222-*a* is configured to build a text message after receiving a response from response queue 225. For example, text worker 222-*a* can be configured to fetch a text template from a store (e.g., response store 237) based on the information in the response to build the text content of the text message. Text worker 222-*a* can also be configured to include the text from the response in the text content of the text message. Text worker 222-*a* can further be configured to include the information of the user's mobile phone number, the user specific messaging application and account information, from the user's profile stored at profile store 239 to fully compose the text message, and send it through, for example, Twilio service.

In some embodiments, email worker 222-*d* is provided by running an instance of an application that generate the desired message types, such as running a Gmail® application, Microsoft Outlook®, any other type of email application; or by accessing a cloud-based email service (e.g., Amazon Simple Queue Service). The email message may be generated to be appropriately formatted for specific messaging platforms, for example and without limitations, Gmail client, Outlook 365, Outlook Web Access (OWA), Webmail, iOS, and the like. In some embodiments, email worker 222-*d* is configured to build an email message after receiving a response from response queue 225. In some embodiments, email worker 222-*d* is configured to use the information in the response to fetch a template from a data store as the detail page of the email message, and use other user specific information to populate the detail page, put headers (e.g., sender's email address, user's email address, subject line, priority level, etc.) to the email to fully compose the email message. Afterwards, email worker 222-*d* is configured to utilized one or more email servers to send the email to the user. In some embodiments, email worker 222-*d* is configured to include information that is entered by a service professional or otherwise generated by platform 206 for being included in the response into the detail page.

In some embodiments, website worker 222-*n* Is configured to furnish a landing page upon, for example, the user clicking on a link included in a text message or an email message, or otherwise interacts with the content sent to them. In some embodiments, website worker 222-*n* is configured to retrieved the landing page from a template page store (not shown) In some embodiments, website worker 222-*n* is configured to track information such as what browser the user is using when interacting with a link, which web content the user interacts once traversing to the landing page, and so on.

Conversation management module 212 includes a classify and summarize sub-module 231, a conversation tracker 232, a workflow manager 233, a ruleset store 234, a real-time processing sub-module 235, a scoring and classification sub-module 236, a response store 237, and profile store 238.

In some embodiments, conversation management module 212 is configured to receive user input (e.g., input sequence) from message executing module 210. In some embodiments, classify and summary sub-module 231 receives the user input from router 224 of message execution module 210. After the analyzing (e.g., identifying, classifying, summarizing, scoring, and/or ranking, etc.), the user input, and/or the analysis results are forwarded to workflow manager 233. In some embodiments, classify and summary sub-module 231 intelligently analyzes use input by applying automated AI classification and/or reasoning techniques. For example, classify and summary sub-module 231 can resolve ambiguities, infer a context to achieve improved understanding of the user's goal, intent, information meant to be provided with respect to the communication. In some embodiments, classify and summary sub-module 231 applies speech recognition, natural language processing, and/or AI techniques to interpret the user input and determine the user's likely intent, goal, or information meant to be provided with regard to the current communication at platform 206. By invoking real-time processing sub-module 235, classify and summary sub-module 231 analyzes the user inputs in a real time manner. By invoking scoring and classification sub-module 236, classify and summary sub-module 231 classifies the user inputs with a confidence score. Based on its processing of the user input, classify and summary sub-module 231 looks for one or more elements that trigger a change in a workflow, such as information relevant to the values of the variables specified in the ruleset, which is determined based the service type determined by router 224, likelihood of seeking a service other than the present one, likelihood of seeking a specific sub-specialty of the present service, and the like. In some embodiments, such elements are not present in the user input and there is no need to modify the workflow. In some embodiments, such elements are determined based on the answers the user provides to surveys conducted in one or more steps of the workflow. In some embodiments, classify and summary sub-module 231 processes the user input using the user profile information stored at profile store 238. This way, classify and summary sub-module 231 determines that the user input may have different meanings depending on the user's context information, such as the user profile information, previous communication of the user at platform 206, on-going communication related to other services at platform 206, and the like. In some embodiments, probabilistic or statistical models (e.g., Bayesian modeling) are used to compute the likelihood, probability, or degree of confidence or certainty with which the user input can be associated with a particularly intended meaning based on the user profile. For example, certain user input may have a different meaning depending on whether the user is travelling (out of town) or at home base (in town), whether the user has experienced a major life event (a first newborn child), whether the user has requested the same type of service before, if so, how long ago, and the like. In some embodiments, classify and summary sub-module 231 determines that the user input may have different meanings depending on the information and data of other users. For example, given a particular timing and geo-location, classify and summary sub-module 231 determines that an user input of "coughing" may have a meaning of "coughing because of the air pollution caused by forest fires" based on the observation of the communication from other users in the same geo-area and around the same period of time, instead of "coughing because of a cold" in other contexts.

After receiving the user input and/or the analysis results, workflow manager 233 is configured to, for example, associate a workflow with the user, and in turn communicate with internal UI 214 so that the user's inputs and respective workflow are displayed and controlled via internal UI 214 (e.g., Workflow Controller 242). Internal UI 214 can indicate that a workflow has been provisioned with a chatbot which has started conversing with the user; or the workflow awaits the handling by either by an agent (e.g., a professional, or an administrator) of platform 206. More details are described below with reference to FIG. 4A-G.

Conversation tracker 232 is configured to keep a record of all the communications exchanged between the user and platform 206. In some embodiments, conversation tracker 232 can store all the non-HIPAA related communication and data in one data store (e.g., conversation history 261 of FIG. 2B-1), and all the HIPAA related communication and data in another data store (e.g., Jiseki HIPPA data store 255 of FIG. 2B-1). In some embodiments, conversation tracker 232 further separately stores all the responses generated at platform 206 in response store 237. In some embodiments, conversation tracker 232 further separately stores all the inputs generated from the user at, for example, a Jiseki analytics store 267 of FIG. 2B-2. In some embodiments, conversation tracker 232 communicates with third party services 216 so as to record the communication between the user and third party services, and the communication between platform 206 and third party services 216. In some embodiments, Conversation tracker 232 communicates with internal UI 214 (e.g., dashboard 241) so that internal UI 214 can access all the communication and data related to the user, platform 206 and third party services.

Workflow manager 233 is configured to associate a workflow with the user request based on the determined service type and the user profile information. In some embodiments, based on the service type and/or profile information, workflow manager 233 identifies a ruleset corresponding to the token include in the user input. For example, upon receiving #doc, a general clinical ruleset is retrieved from ruleset store 234, and applied to rule engine 218 for evaluation, the output of which produces a corresponding general clinical workflow (using the steps in response store 237). In this example, the ruleset indicates for a general medical questionnaire to be presented to the user by a chatbot, if no preference is specified otherwise. Rule engine 218 evaluates the ruleset using the profile information and the user input information. If either one including an element that indicates the preference as "non bot," rule engine 218 outputs a workflow of presenting the medical questionnaire by an agent. Otherwise, rule engine 218 outputs a workflow of presenting the medical questionnaire by a chatbot.

In some embodiments, rule engine 218 evaluates a default ruleset using the WPC scorings stored in the profile of the user prior to evaluating a ruleset corresponding to the identified service type in order to generate a workflow. For example, a rule in the default ruleset can specify to always apply the rulesets of the categories having a higher scoring sooner than those having a lower scoring. For another example, a rule in the default ruleset can specify to generate a workflow for following up with the user in a particular category, other than the requested service type and with a scoring exceeding a pre-configured threshold, in addition to generating the workflow responding to the requested service.

Workflow manager 233 is also configured to modify the workflow associated with the request based on the user inputs and the user profile information. In some embodiments, workflow manager 233 first identifies a corresponding ruleset addressing the determined service type from ruleset store 234. Next, workflow manager 233 applies the obtained ruleset to rule engine 218 so as to obtain a workflow of steps, which are identified from a reservoir of existent steps (e.g., response store 237). In some embodiments, the service request is sufficiently specific (e.g., #dentist) to be used to retrieve the specific corresponding ruleset. In some other embodiments, a service request is relatively general (e.g., #doc, #sore throat), then a corresponding high level ruleset is retrieved accordingly. In some embodiments, a high level ruleset is implemented in a recursive structure (e.g., a tree structure) so that the execution of the steps in the workflow determined based on the high level ruleset (e.g., general medical ruleset) leads to identifying the next level ruleset, and so on. For example, the execution of a step of the initially identified workflow leads to the gathering of new user input (e.g., answers to newly identified surveys or questionnaires) and information derived therefrom, which further leads to rule engine 218 identifying other rulesets upon evaluating the high level rule with the new user input and information. For example, upon executing a step of a workflow associated with a general medical service request (#doc), a ruleset addressing medical specialties (#rhinosinusitis) can be identified for subsequent evaluation by rule engine 218. Furthermore, modified workflows can be stored in response store 237.

Once a workflow is associated with the user request, workflow manager 233 is configured to execute the steps of the workflow accordingly. For example, for an automation step, workflow manager 233 will deploy a correspondent chatbot or AI assistant according to the communication mode, type, and priority specified for the step. For a step that needs service professional's handling, workflow manager 233 queues the respective user request to a list and causes internal UI 214 to update the display of the list accordingly so that professionals can claim the user request off the list via internal UI 214. For a step to wait for an ordered lab results, workflow manager 233 causes internal UI 214 to alert the professional once the lab results become available. In some embodiments, workflow manager 233 is further configured to automatically flag a user request to better describe/capture the nature of the request. In some embodiments, internal UI 214 allows professionals to add and remove flags in association with a user's request. Upon completion of all the step in a workflow, workflow manager 233 dis-associates the workflow from the user request.

Workflow manager 233 also communicates with workflow tracking 245 of internal UI 214 so that professionals at internal UI 214 can access, view, flag, group, and operate on workflows associated with various users' requests in suitable manners. Once a workflow is associated with a user request, all the information of the workflow is relayed to internal UI 214 for display. For example, a mental health care professional can access all the chats exchanged between Sara (AI assistant) and the user who is seeking mental health related help at platform 206 before deciding it is the right time to take over the conversation. Workflow control 242 of internal UI 214 communicates with ruleset store 234 so that professionals at internal UI 214 can manually engage the user to carry out one or more steps, provision the workflow for execution by other professionals and/or chatbots, modify the ruleset, modify the workflow, release the workflow from association with the user request, and the like. For the workflows that are manually modified by professional via internal UI 214, the underlying pattern can be captured in terms of updates to the ruleset corresponding to the workflow, updates to the diagnostic questionnaires related to the ruleset, as well as updates to the domain knowledge base at platform 206.

A workflow is a collection of steps corresponding to a chain of events and processes/actions starting from a first engagement (e.g., an intake) of a user who sends a request for a service, until the requested service is fulfilled and the user released from the workflow. Taking medical or clinical services for example, a medical workflow may include a set of one or more steps (ordered or not, or partially ordered) that encompass a patient intake with pertinent diagnostic processes (e.g., questions, lab orders, modality orders, and the like); diagnosis of a condition; treatment (e.g., prescription of medication treatment, physical treatment, and the like) of a condition; follow-ups; etc. The workflow oftentimes entails cooperation of a variety of entities such as automation entities (e.g., smart bots, chatbots, AI assistants), human professionals or agents (e.g., doctors, clinical staff, nutrition advisors, physical therapists, mental health care providers, pharmacist), third party services (e.g., payment service, online prescription services), as well as involving a large amount of data and information.

Steps of a workflow correspond to specific tasks/actions to be performed during the course of delivering the service based on the workflow. For example, diagnosis of a condition can be performed by a step of activating a chatbot equipped with the corresponding diagnostic questionnaire (further including a step of platform 206 providing a link to a HIPAA compliant platform on which the chatbot is to engage the user), and/or a step of facilitating the user making an appointment with a selected medical doctor (further including a step of platform 206 providing a link to a calendar service, and/or a payment service). For another example, treatment can be performed by a step of a chatbot sending the user a care plan (e.g., when simple home remedy seems sufficient based on the diagnosis), a step of platform 206 providing the treating doctor with an online prescription service to prescribe medication for the user, a step of platform 206 allowing the doctor to send the user emails, documents (e.g., educational materials), a step of a chatbot reminding the user to take the medication timely, and the like.

In some embodiments, steps of workflows are indexed to the respective action or event type. For example, a step of generating a HIPAA compliant communication link for embedment into a SMS message to the user is indexed under, e.g., HIPAA link. For another example, once platform 206 narrows down the user's request from a relatively general one (e.g., #doc) to a relatively specific one (e.g., sore throat, flu) after obtaining more information from the user (e.g., by conducting diagnostic questionnaire guided communication, which is described with more details below), a step of a chatbot sending the user a care plan is mapped to the chatbot sending a care plan specific to the identified narrowed request.

In some embodiments, each step of a workflow corresponds to at least one of the following attributes: communication modes, communication types, and communication priority. Communication modes include, for example, text, voice/video call, HIPAA compliant versions of text and voice/video call, and web form, etc. Communication types include, for example, conversation initiated by professionals such as doctors and nurses, bots, or AI assistants. Communication priority includes, for example, a level of priority associated with the user in terms of how soon platform 206 is expected to execute the requested services to the user. As further illustrated with reference to FIGS. 7A-B, steps of a workflow are performed by a combination of chatbots, AI assistants, and professionals.

In some embodiments, workflows are determined based on the results of rule engine 218's evaluating of one or more rules included in a ruleset corresponding to the service request. In some embodiments, a workflow is modified by workflow manager 233 based on inputs from the user, and/or the user profile information. In some embodiments, a workflow is provisioned and/or modified by workflow manager 233, based on information and data observed and derived at platform 206, from communication between platform 206 and other users. Workflow manager 233 can add one or more steps to a workflow, delete one or more steps from a workflow, expand a step into multiple steps, modify the attributes specified at one or more steps of a workflow, and the like.

In some embodiments, changes captured in the user profile information triggers workflow manager 233 to modify the step attributes, and/or re-apply rulesets to rule engine 218 with the updated variable value. For example, the user profile information is updated based on a newly shared note from a mental health care professional indicating that a user is not friendly when talking to a chatbot. In some embodiments, the update is captured in an increased score related to the preference category. The increased score triggers workflow manager 233 to check whether any workflow is currently being executed in connection to any request from the user. If any, workflow manager 233 is triggered to modify the steps to be performed by chatbots to steps awaiting professional processing. For another example, the user profile information is updated by a newly received lab report that a user is diagnosed with hypertension and therefore might be in heightened need of mental health related care. In some embodiments, such update is captured in an increased score related to the mental health state category. The increased score triggers workflow manager 233 to check whether any workflow is currently being executed in connection to any request from the user. If any, workflow manager 233 is triggered to re-apply the ruleset(s) respective to the workflow(s) to rule engine 218 to determine whether the workflow(s) is to be modified based on the profile update. In this case, based on rule engine 218's re-evaluation of the ruleset, a step is added to the workflow (which is responsive to a non-mental health care related request) so that a chatbot can proactively reach out to the user, either during the course of executing the workflow, or upon the completion of the workflow, with regard to an assessment of mental health wellness (using a survey pre-configured with the step).

In some embodiments, information obtained from the input sequence from the user during the execution of a workflow also triggers workflow manager 233 to modify the workflow. For example, based on the previous and ongoing conversations, it is determined that the user is likely in the middle of a crisis (e.g., based on the medical topic on which services have been requested, the frequency of the related requests, the nature of escalating issue related to the requests, detected user's mood, etc.). As such, the detection triggers workflow manager 233 to modify the communication priority for the steps of the workflow associated with the request.

In some embodiments, information observed, derived, learned from communication and data transacted at platform 206 is captured as updates to rulesets corresponding to user requests. In this case, changes in the rulesets triggers workflow manager 233 to check whether any workflow determined based on the pre-update ruleset is currently being executed in connection to any request from the user. If any, workflow manager 233 is triggered to re-apply the ruleset(s) to rule engine 218 using the latest ruleset to determine whether the workflow needs to be modified based on the ruleset changes. For example, a ruleset responding to a veterinary service request is updated to change the recommended flea control medication for pets from brand A to brand B only in a particular geo-area based on the communication and data transacted on platform 206 related to pet flea control requests. As such, workflow manager 233 is triggered to re-apply the updated ruleset to all the pending requests related to pet flea control in that geo-area. In some embodiments, the afore-described information is captured in the ruleset in the form of instructions for rule engines 218. For example, a change in the instruction can cause rule engine 218 to ignore the order of evaluation based on the orders of the scorings in various categories (e.g., categories in the WPC survey), and instead to evaluate the rulesets in a category with a lower user score sooner than the rulesets in a category with a higher user score.

Domain knowledge is used to generate rulesets and diagnostic questionnaire. Domain knowledge includes information such as medical knowledge, financial knowledge, mental health wellness knowledge, and the like, and is stored in one or more databases (not shown). Domain knowledge can also be retrieved from third party databases of hospitals, healthcare facilities, and research facilities. Domain knowledge can also be derived and/or self-compiled based on the communication and data transacted at or available to platform 206. In other words, domain knowledge utilized by platform 206 can be expanded, updated and developed based on the information gleaned, accumulated, and/or conducted by machine learning techniques through servicing a variety of users in a variety of service.

In some embodiments, steps of workflows are also generated based on domain knowledge, such as clinical protocols, guidelines and best practices (e.g., established standards), in relation to conditions users may be suffering from or issues (e.g., financial issues, diet issues, mental health issues, etc.) on which they are seeking service/help at platform 206. In some embodiments, based on the knowledge/understanding of user profile information (e.g., user preferences) gathered through a whole person care (WPC) survey, previous conversation on the same channel and/or interactions on other channels, the workflow and its steps (e.g., modes of communication, and types of communication previously associated with the user) can be dynamically provisioned and/or modified during the delivery of the requested service.

For example, medical guidelines, protocols, best practice knowledge can be used as medical domain knowledge, thereby forming the basis to generate rulesets and corresponding diagnostic questionnaires that are invoked in response to a user's request for clinical services. In some embodiments, transforming and/or mapping the guidelines, protocols and best practice knowledge into rulesets and diagnostic questionnaires can be performed by human operators (e.g., Jiseki engineers). In some embodiments, such transforming and/or mapping can be performed automatically and/or reviewed by human operators, using techniques such as artificial intelligence, and the like. In some embodiments, domain knowledge based rulesets and diagnostic questionnaires can be obtained from third party providers.

Taking an upper respiratory tract infection (URTI) condition for example, a diagnostic questionnaire is promulgated based on the domain knowledge obtained from various sources (e.g., private practice, clinics, guidelines, etc.) to include nine ordered questions. In some embodiments, the questions are designed and presented as either "yes" or "no" questions, multiple choice questions, or any combination thereof, to better accommodate online communication (e.g., web browser based or SMS based messaging, voice based messaging). In some embodiments, the diagnostic questionnaire is further enabled with tools/widgets/links for the user to transmit information and data other than text or voice or video communication. For example, one question included in the URTI questionnaire provides a set of instruction on how to take a picture at the back of the user's throat, and a link for uploading the picture taken.

In this example, the questions are presented to the user at a HIPAA compliant platform in response to the user's service request (e.g., #cold, #flu, #stuffy nose, #sorethroat, etc.). The questions are presented in an order of from question 1 to question 9 so that, when the user answers one of the questions in a certain way, the flow of the question either stops (done with gathering sufficient information), or branches to all or some of the remaining questions. For example, only when the user answers "yes" to question 1, "no" to question 2, and "yes" to question 5, question 7 is presented to the user. In general, the questions at the beginning of the set tend to gather information about the general aspects of the condition (e.g., running nose, cough, sore throat, fever), and the later questions tend to gather information about aspects more specific and responsive to the information obtained through the previous questions (e.g., smoking history).

Still in the URTI example, the answers to the respective questions in the diagnostic questionnaire are assigned with a score, and an overall scoring corresponding to the user's answers to one or more questions are computed. Based on comparing an overall scoring with a pre-configured threshold, a diagnosis can be formed in turn. For example, if the user's answer scores equally or greater than a threshold pre-configured in reference to question 4, question 6 and question 7, the user's condition is diagnosed as flu. For another example, if the user's answer scores equally or greater than a threshold pre-configured in reference to question 3, question 2 and question 5, the user's condition is diagnosed as sore throat. In the instant case, if the user answers "yes" to the question about a history of fever, one positive score is assigned to the answer; if the user answers "no" to the question about the presence of coughs, one positive score is assigned to the answer; if the user is older than 44, one negative score is assigned to the answer; and if the user is younger than 15, one positive score is assigned to the answer. Then, an overall scoring is computed based the scores. If the overall scoring is between 0-2, it is concluded that the user should be treated with a low likelihood of group A strep condition; if the overall scoring is between 3-4, it is concluded that the user should be treated with an intermediate likelihood of group A strep condition; and if the overall scoring is greater than 4, it is concluded that the user should be treated with a high likelihood of group A strep condition. In some embodiments, the scores are weighted based on other factors such as age, geo-locations, other known medical conditions, financial status, and the like. In this scenario, an overall scoring is computed based on both the score and its respective weight.

Still yet in the URTI example, based on the domain knowledge that generates the design of diagnostic questionnaire, as well as the pre-configuration of scores and their respective weights for association with various questions in the diagnostic questionnaire, a ruleset corresponding to processing an URTI related service request is generated and stored in ruleset store 234. The ruleset includes the one or more branching conditions (scores and/or overall scoring with regard to answers to particular questions, overall scores) contributing to the diagnosis of flu, sore throat, common cold, and rhinosinusitis, as well as the levels of likelihood the user is infected with group A prep. In the instant case, various scores and/or scoring constitute variable values in a rule, various pre-configured thresholds constitute constant values in a rule. For example, a rule in the URTI ruleset can specify that, if the scores/overall scoring are greater than a pre-configured threshold indicating a condition of flu, include a step of a chatbot sending a correspondent care plan to the user, and include a step of a chatbot to follow up with the user after a pre-configured period of time. Another rule in the URTI ruleset can specify that, if the scores/overall scoring are greater than a pre-configured threshold indicating a condition of rhinosinusitis, include a step of setting up an appointment with a medical doctor, and include a step of a chatbot to follow up with the user at a time after the appointment.

Ruleset store 234 includes a plurality of rulesets corresponding to responding to service requests of the user. A ruleset can be indexed under one or more corresponding service types (e.g., general type such as #doc, specific type such as # rhinosinusitis). A ruleset contains one or more rules, which are evaluated by rule engine 218. After making its evaluation, rule engine 218 provides the result of its evaluation as output. The following is an example of a rule: if (score>8) and (score_y<6) then a; else if (score_x<4) then b; else c. A clause of a rule (e.g., if (score_x>8) and (score_y<6) then a) includes one or more conditions, one or more conjunction (and, or, and not, or not), a connector (e.g., if, lese if, else), and provides one result. A condition includes two arguments, which may be both variables, or one variable and one constant. A condition includes one comparison evaluator (equal to, greater than, contains, etc.), and can further includes one or more conjunctions (and, or, and not, or not). A variable list includes one or more pairs of a variable name and variable value. Variable values are substituted into variables in arguments of conditions.

In some embodiments, variable values are obtained from the scores and/or scoring of user's answers to various diagnostic questions. In some embodiments, variable values are further obtained from the scores/scoring stored in a profile of the user. Likewise, a rule can further specify at a finer granularity with regard to the conditions. Taking the rhinosinusitis related rule of URTI ruleset for example, the step of a chatbot to follow up with the user at a time after the appointment can be further specified as, if the user profile indicates a tendency of being good-natured upon a human conducting a follow up, include a step of a human agent to follow up with the user; otherwise, include a step of a chatbot to do so. In some embodiments, a rule of a ruleset can also specify to evaluate one or more other rulesets upon the condition been met.

In some embodiments, a ruleset addressing a service topic (e.g., cold) can include proactive rules that allows platform 206 to reach out to the user to raise awareness/concerns about potential issues in the service areas other than the specific topic (e.g., another medical specialty, financial issues). For example, a rule in the URTI ruleset can specify that, if the user's profile indicating a change of condition, e.g., newly diagnosed hypertension, include a step of reaching out to the user with mental health concerns. Such condition can be captured in a user's replies to a recent survey, or the user's lab results coming back to platform 206 confirming a condition of hypertension.

Rule engine 218 performs evaluations of the rules of a ruleset in rule set store 234 by first substituting values into variables, then evaluating each condition of a clause, determining a result for each clause, and finally determining a result for the entire rule based on the results of the clauses. Rule engine 218 is configured to access ruleset 234 and response store 237, which store steps that can be assembled for each workflow. In some embodiments, rule engine 218 are implemented using various techniques, such as Drools, JEOPS (Java Embedded Object Production System), OpenRules, etc.

In some embodiments, various surveys are conducted at platform 206 also for the purposes of generating rulesets and corresponding diagnostic questionnaires, as well as gathering and/or updating the user profile information. For example, when subscribing to and/or logging for the first time onto platform 206, the user is presented with a whole person care (WPC) survey. A WPC survey can be designed to gather user information on various categories, such as medical and wellness states, financial state, mental health state, household conditions, etc. In some embodiments, WPC scorings can be computed to assess triage factors for each category. Similar to the scoring described above, a score and its respective weight is assigned to various answers in categories from the user to a question. For example, for question that "when do you last see your primary care or nurse practitioner," answers of "3 months ago," "6 months ago," "a year ago" are assigned with a pre-configured score, respectively. Then, an overall scoring under each category is computed and stored in a profile associated with the user, representing a corresponding status factor. In some embodiments, periodical surveys, varying timing and topics, in one or more particular categories are sent to the user to gather new and/or updated information. In some embodiments, content and schedules of periodical surveys are customized according the profile of the user, communication of other users, and the like. The results returned by the user or the lack of returned results are similarly scored so as to update the overall scoring in each category in the profile of the user. In some embodiments, the WPC scorings are updated based on communication and data available at platform 206 in relation to servicing the user, and/or a group of users. All the scores and scorings stored in the user profile can be utilized by rule engine 218 to evaluate rules that condition on such scores and scorings.

A "profile" as used herein, refers to a collection of information, observed or derived, about a user. A profile may include static data that is not likely to change over time, and dynamic data that are likely to change over time. For instance, a profile may include demographical data (retrieved from a demographic data store 239-1), subscription data, medical data (retrieved from an EMR store 239-2), financial data (retrieved from a financial data store 239-3), social media data (retrieved from a social media data store 239-n), user biometric data, user relationship data (family information, social network information, professional network information, relationship status, life events), user geo-presence data (residency location, nationality, travel routes), and the like of the user. A profile may also include preferences of the user, either specified by the user, or observed or derived from the user's communication and behaviors at platform 206. A profile may also include WPC scoring computed and adjusted over time for the user. A profile may also include notes and observations various chatbots, AI assistants, and professionals attached to the user via internal UI 214. A profile may also include user environment data such as information about the user's device, user' application data (e.g., calendar entries), etc. A profile may also include data from third party service provided to platform 206 (e.g., lab results, imaging results). A profile may also include a machine learning and/or AI model that classifies intents, goals, moods of the user, determines the real meaning/semantic meaning of the user on the user's input communication, or other users' communication. In some embodiments, the user profile information is bifurcated into two categories: HIPAA sensitive or non-HIPAA sensitive for storage at separate data stores with appropriate security and privacy guards.

In some embodiments, conversation management module 212 is configured to, for example, classify, summarize, profile, rank, score, track the conversation, both in real time style via, for example, scoring and classification sub-module 236 and real-time processing sub-module 235, and non-real time style, in order to both provision and modify the message-based service for delivery, in real time or non-real time manner. In some embodiments, processing, scoring, ranking functionalities sits behind workflow manager 233, determining whether the workflow needs adjustment.

Internal UI 214 includes a conversation dashboard 241, a workflow control 242, a tags sub-module (e.g., a tagging sub-module) 243, a note sub-module (e.g., a note-taking sub-module) 244, and a workflow tracking sub-module 245. In some embodiments, conversation dashboard 241 is configured to communicate with conversation tracker 232 of conversation management module 212, which communicates with router 224 of message execution module 210. In some embodiments, workflow control 242 is configured to communicate with ruleset store 234 of conversation management module 212. In some embodiments, workflow control 242 allows professionals manual interaction with the workflow (add a step, delete a step, modify a step, etc.); in some embodiments, it also allows professional to change and store the ruleset corresponding to the workflow for the user. More detail of internal UI 214 is described below with reference to FIGS. 4A-G.

In some embodiments, platform 206 enables Jiseki administrative/engineering personnel to manage various aspects pertaining to professionals (e.g., agents) and administrators accessing platform 206. For example, a Jiseki super administrator can organize the services available at platform 206 into domains based on a variety of criteria. For instance, domains can be assigned based on geo-locations so that services provided to users residing in one neighborhood, city, county, or the like can be aggregated in one domain. Alternatively, services provided to users communicating via a group of one or more chatbot servers can be aggregated in one domain. Domains can also be based on the types of services, such as clinical, financial, mental healthcare, specialty of service domains (e.g., tax, URTI (upper respiratory tract infection)), and the like. One domain can be further organized into subordinate domains depending on the granularity deemed necessary or appropriate for delivering services at platform 206. For another example, a Jiseki administrator can create and manage various flags for association with communication. For instance, a request for and communication related to a financial service can entail flags related to credit card service (e.g., #card flag), financial advisor service (e.g., #money flag), and the like. For an agent tasked with handling medical related requests, such agent is further authorized to access only medical related flags, but not the communication flagged under legal or financial services. For yet another example, in addition to creating and managing accounts for individuals to log on, a Jiseki administrator can authorize different access privileges to the communications available at platform 206 by assigning correspondent roles to the individual accounts. For instance, a Jiseki administrator can create roles under which a collection of functionalities/actions can be performed by the role holder. For example, an individual can be assigned a role of: admin, super admin, agent, concierge, financial, MCD, MCD concierge and talk, medical—Rx, mental health agent, and the like. An individual assigned with an administrator role at a particular domain is able to access all the communication (e.g., chats) and flags in that domain. Such individual can also create and manage flags associated with the domain, as well as create and manage accounts of other individuals servicing the domain (e.g., grant authorization to access HIPAA sensitive data stores). An individual assigned with an agent role at a particular domain can view the flags in the domain, request for new flags to be created, and access the communication (e.g., chats) in the domain. An individual at a super admin role has all the rights and privileges of administrators across all the domains. With the organized domain structure, role assignment and flags assignment, platform 206 is able to scale effectively and efficiently despite a large amount of user requests and interactions transacting thereat.

In some embodiments, platform 206 is a configured for creating, modifying, and managing workflows, using AI-based schemes (e.g., intelligent processing/analysis, machine learning, etc.) such that to perform and/or assist service provisioning and modification for the purposes of delivering message-based services. Artificial intelligence (AI) refers to computer systems which exhibit intelligent behaviors including, for example and without limitations, the capacity to observe, learn, maintain a large store of data and knowledge; apply the abilities of reasoning, analyzing, inferring, summarizing, ranking etc. to data and information, discern relationships between data and information; understand, perceive and make sense of data and information within the context, as well as communicate information (e.g., propose, suggest, or recommend). In some examples, artificial intelligence systems create new knowledge, insights, best practices by finding previously unknown patterns in data, and delivering new solutions by learning patterns in data.

Figures 1, 2B:
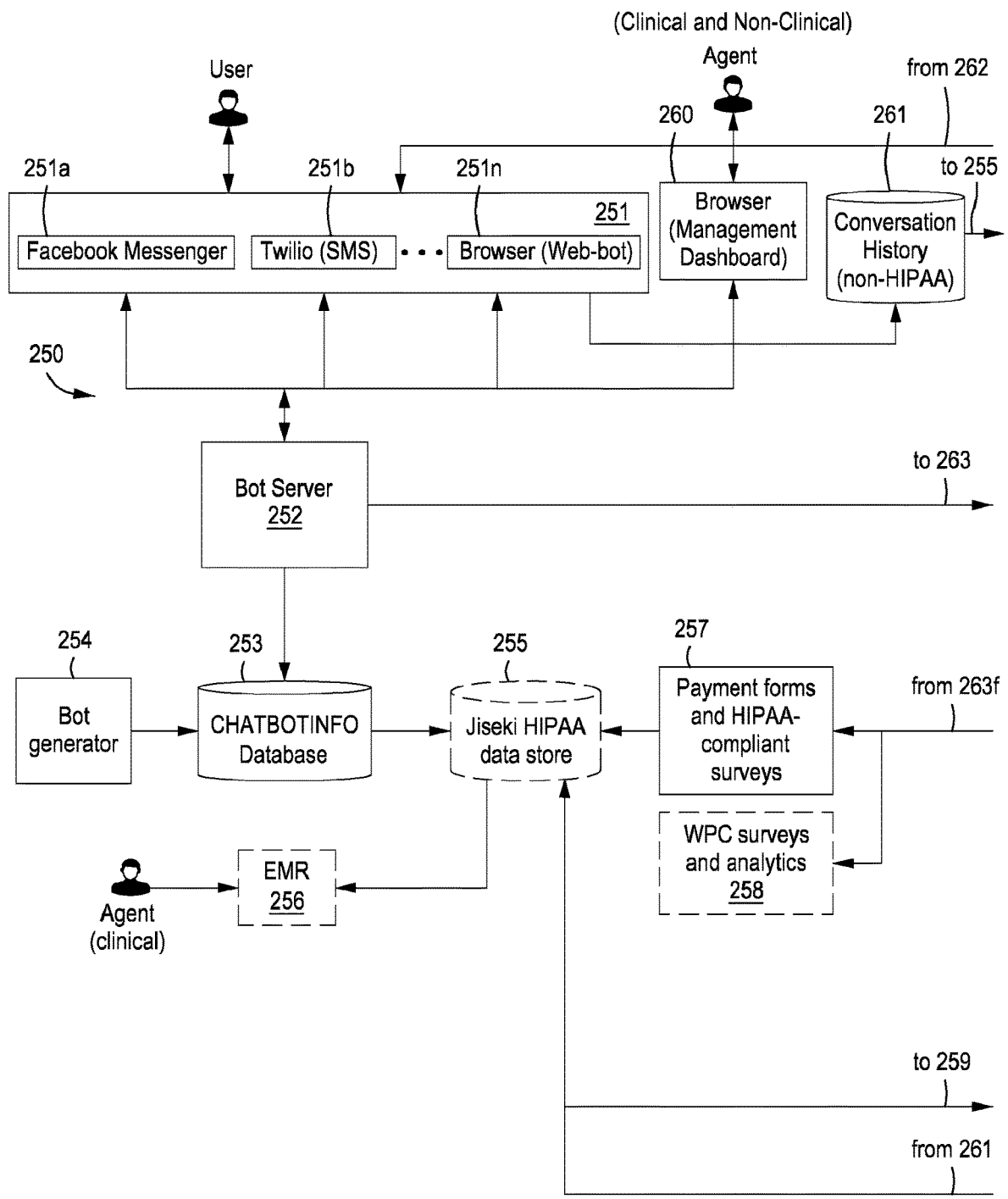
FIGS. 2B-1 and 2B-2 are another simplified example block diagrams of some of the architecture of a system for AI assisted service provisioning and modification for delivering message-based service in accordance with one or more embodiments of the present disclosure.

In some embodiment, conversation management module 212 is configured with smart bots (not shown, and such as smart bots 109a of FIG. 1A, as well as bots executing on bot server 252 of FIG. 2B-1), and/or AI assistant (not shown, and such as AI assistance 109b of FIG. 1A, as well as third party service 263-a of FIG. 2B-2) which can assess and/or be trained by data such as data of the user in a profile store 238, content of the conversation from both the user and platform 206 and/or service professional (e.g., data in response store 237, data in conversation history 261 of FIG. 2B-1, JISEKI HIPAA data store 255 of FIG. 2B-1), data obtained from, derived from, or pertaining to the afore-described features to classify, summarize, profile, rank, score, track of conversations, in relation to a single channel conversation (e.g., related to one type of service) of a same user, multiple channels conversation (related to multiple types of services) of the same user, and/or any channel conversation of different users. In some embodiments, the training of bots/AI assistants is implemented at the level of ruleset, e.g., the rulesets in ruleset store 234 (e.g., analytics store 267 of FIG. 2B-2) are trained with the afore-described information and data so as to dictate the corresponding workflows carried out bots/AI assistants/professionals. In some embodiments, user profile information and/or classify and summarize sub-module 231 are created, updated, and/or managed by AI models trained with the afore-described information and data.

Moreover, various AI-based methods or machine learning methods can be generated, managed, and maintained at platform 206. Artificial intelligence techniques can typically apply advanced mathematical algorithms, e.g., decision trees, neural networks, regression analysis, principal component analysis (PCA) for feature and pattern extraction, cluster analysis, genetic algorithm, or reinforced learning—to a data set. In particular, platform 206 can employ one or more of methodologies for learning from data and then drawing inferences from the work flow models constructed. For example, Hidden Markov Models (HMMs) and related prototypical dependency models can be employed. General probabilistic graphical models, such as Dempster-Shafer networks and Bayesian networks like those created by structure search using a Bayesian model score or approximation can also be utilized. In addition, linear classifiers, such as support vector machines (SVMs), non-linear classifiers like methods referred to as "neural network" methodologies, fuzzy logic methodologies can also be employed.

Furthermore, it should be appreciated that the neural networks used by platform 206 are artificial neural network implementations, which include one or more neural networks such as a feedforward neural network, a radial basis function network, a convolutional neural network, a recurrent neural network, a cascading neural network, a spiking neural network, a neuro-fuzzy network, or any other type of neural network implementation. For example, with each new pair of user input and one or more responses recorded at response store 237, the neural network layers of classify and summarize sub-module 231 get more precise to identify the intent, goal, information meant to be communicated by the user, thus facilitating platform 206 to select, provision, and/or modify workflows to better service the user.

In some embodiments, classify and summarize sub-module 231, as well as AI models for creating, refining, updating, and/or managing rulesets in ruleset store 234 and/or profiles in profile store 238 can be explicitly trained (e.g., via identified training data), implicitly trained (e.g., via observing communications, preferences, historical information, receiving extrinsic information such as social media data, user device data, user calendar data, user biometric data, user environment data, etc.), as well as trained in a hybrid manner (e.g., both explicitly and implicitly). For example, SVMs can be configured via a learning or training phase within a classifier constructor and feature selections. Thus, classify and summarize sub-module 231 can be used to automatically learn and perform a number of functions, comprising but not limited to determining according to a predetermined and/or learned criteria, priority, user goals, user intent, and/or user situations, a set of one or more services that can be utilized to accomplish the user goal, a subset of services, resources to establish a selected service, etc. The criteria can comprise, but is not limited to, user profiles, historical patterns and/or trends, service provider preferences, predicted traffic flows, event data, current time/date, contact list data, subscription data, location data, and so on. AI models in connection to ruleset store 234 may output any information for creating and/or modifying a ruleset in ruleset store 234, such as but not limited to content of the ruleset, attributes associated with the steps of a workflow based on the ruleset, timing associated with the steps of a workflow based on the ruleset, evaluation instruction for rule engine 218. AI models in connection to profile store 238 may output any information for creating and/or updating a profile in profile store 238, such as but not limited to scores respective to categories corresponding to the services available at platform 206, and the like. In some embodiments, a model controller (not shown) determines model parameters when creating a model using a neural network. For example, the model controller specifies how many neurons to be used in the model, how many layers to be used in the model, one or more of an amount of backpropagation, a dimension, and a learning rate with respect to the model. In implementation, those parameters can be configured as part of a TensorFlow configuration.

In some embodiments, the afore-described training of classify and summarize sub-module 231 and AI models can be conducted iteratively. In some embodiments, those afore-described AI-based schemes are carried out in a real time, near real time, or off-line manner. For example, in some embodiments, classify and summarize sub-module 231 is configured to analyze an input sequence from the user in real time fashion to determine, for example and without limitations, a ranking score in terms of emergency, priority, summarization of user' intent, and the like.

In some embodiments, AI models and classify and summarize sub-module 231 may be trained with data relating to one or more users' communication with platform 206. The training data may take as input any type and form of information related thereto, such as but not limited to, the profiles of the users, the profile of the company/organization of the users, communication content in relation to previously requested same services, communication content in relation to previous services other than the currently requested one, date, temporal, location, and/or timing information, user device information, user social media information, other application information associated with the user (e.g., calendar data), user biometric information, user environment data, etc.

In some embodiments, a combination of AI-based schemes and service professionals is brought into conversations (e.g., message-based service delivery) without interfering with one and other in the course of delivering a service. In some embodiments, such a combination is customized for users based on the knowledge of the users that is accessible or available at platform 206. For example, such knowledge includes the information (e.g., personal data such as gender, birth date, occupation, medical history, financial history, background checks, preferred language for communication, other preferences, etc.) gathered from the user at signing-up (e.g., signed up with the platform directly or through a third party vendor, employer, etc.), through a whole person assessment survey other types of surveys, and the like. The knowledge can also include information supplied from third parties such as credit score of the user, credit/financial history of the user, litigation history of the user, and so forth. The knowledge can also include information such as location, time, event, any contextual information, social media information, user device information, etc. The knowledge can also include information from (e.g., gathered/retrieved/derived from) previous/on-going/scheduled messaging sessions conducted by the user with platform 206. For example, the language preferred by the user for communication. The knowledge from previous/on-going/scheduled messaging sessions can also include information from (e.g., gathered/retrieved/derived from) previous/on-going/scheduled messaging sessions conducted by the user on a channel that provides the same service. The knowledge from previous/on-going/scheduled messaging sessions can also include information from (e.g., gathered/retrieved/derived from) previous/on-going/scheduled messaging sessions conducted by the user on other channels that provide different services. The knowledge can also include information from (e.g., gathered/retrieved/derived from) previous/on-going/scheduled messaging sessions conducted by other users, on the same channel providing the same service, and/or on other channels providing different services. In some embodiments, the workflow is modified based on the knowledge from (e.g., gathered/retrieved/derived from) on-going/scheduled messaging sessions conducted by the user and/or other users, on the same channel providing the same service, and/or on other channels providing different services.

For example, a ruleset corresponding to a mental health service can be trained on data from (e.g., gathered/retrieved/ derived from) the communication conducted by the same user at the channel providing financial service. In other words, platform 206 is configured to cross-train the ruleset with all or a portion of the data that is on (e.g., gathered/ retrieved/derived on) platform 206, regardless of the types of services. Because of the integrated nature of service providing platform 206, better, more accurate, more timely and more comprehensive data is available from across-service sectors to serve as training data for rulesets the platform. In some embodiments, such training data can be further conditioned using profile/status/context/events/statistics and the like. As such, improved and enhanced AI capabilities contribute to provisioning and modifying service workflows in a more accurate, personal, timely and informed manner for the purpose of delivering services. As a result, the improved service provisioning and modification also increases the efficiency and accuracy of the interaction between the user and the professional service providers, reduce the network bandwidth requirement in the system, and reduce the power/ computing resource consumption in the system.

Details of third party services 216 is described below with reference to FIG. 2B-2.

Further, it should be appreciated that one or more of the illustrative components/modules in FIG. 2A may include other components, sub-components, modules, sub-modules, and device commonly found in a communication/computing system, which are not discussed above with reference to Jiseki system and not discussed herein for clarity of the description. Additionally, in some embodiments, one or more of the illustrative components/modules can form a portion of another component/module and/or one or more of the illustrative components/modules can be independent of one another.

Figures 2, 2B:
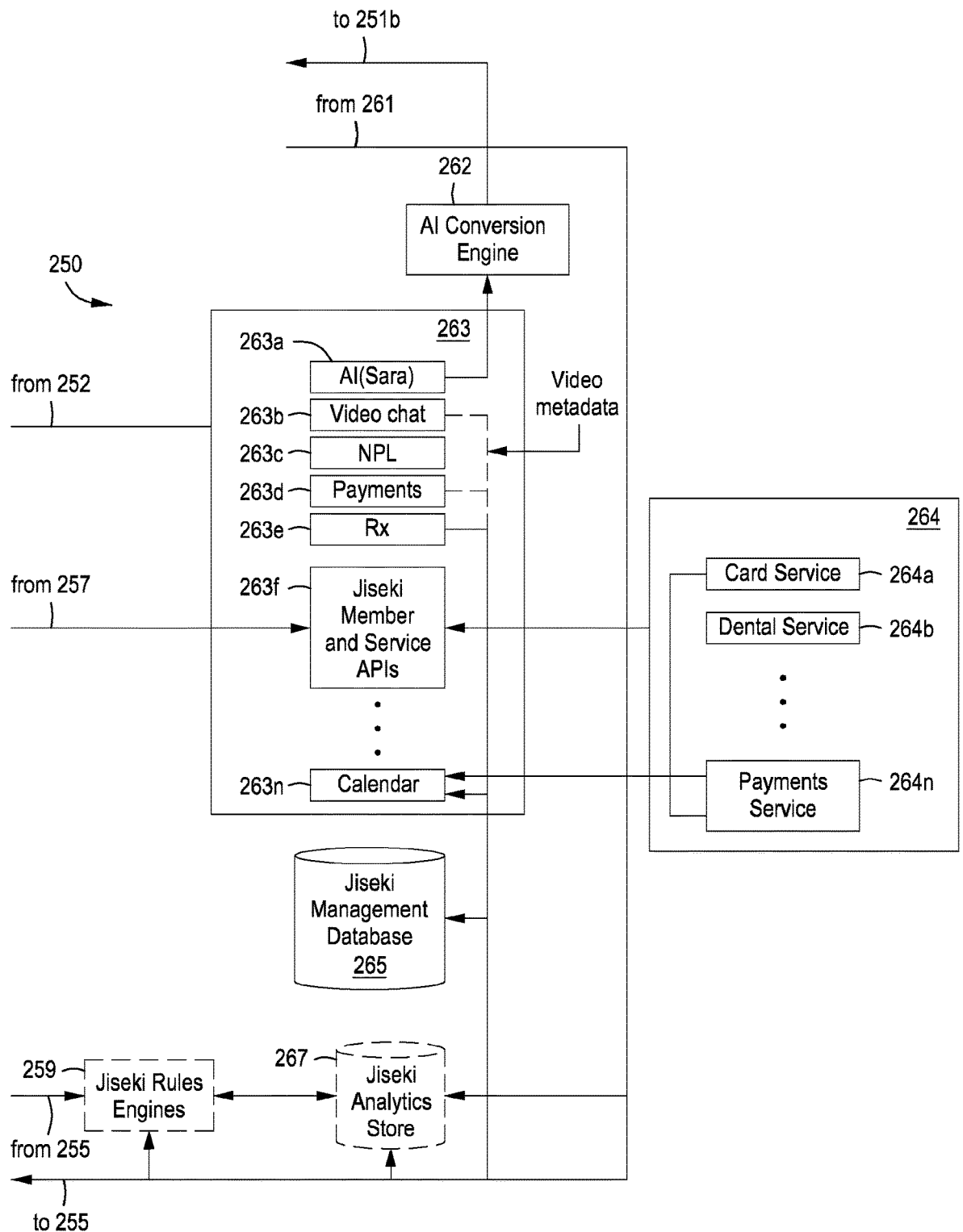

FIGS. 2B-1 and 2B-2 (collectively, FIG. 2B) illustrate another example block diagram of a portion of the architecture of a system for AI assisted service provisioning and modification for delivering message-based service, in accordance with an embodiment of the present disclosure. In this example, system 250 depicts a user 280, an agent (either a clinician or a non-clinician agent) 290a, as well as a clinician agent 290b (collectively agent 290) in communication therewith. User 280 sends inputs to and receives responses from communication module 251. In some embodiments, communication module 251 includes one or more communication portals such as, for example and without limitations, Facebook Messenger 251a, Twilio portal 251b, browser portal 251n, and the like. This way, communications of various modes (e.g., SMS, messaging applications, voice messaging, video messaging, etc.) are enabled and supported between user 280 and system 250. Furthermore, agent 290 connects to system 250 via a management dashboard 260 (e.g., browser), and communicates with user 280 via communication module 251 as well.

Both communication module 251 and management dashboard 260 are configured in communication with a bot server 252. In some embodiments, a conversation history database 261 is configured to record a copy of the non-HIPAA-sensitive content of all or some of the conversations exchanged between user 280 and system 250. For example, conversation history database 261 can record communication between user 280 and chatbots executing on bot server 252, between use 280 and non-clinician agent 290a, between user 280 and AI assistant (e.g., Sara) executing on an AI conversation engine 262, and the like. Similarly, HIPAA-sensitive communication and data related to user 280 is stored separately in a Jiseki HIPAA store 255, which communicates with an EMR store 256.

In some embodiments, bot server 252 is configured to receive from communication module 251 inputs from user 280, and send responses back to user 280 via communication module 251. In some embodiments, bot server 252 is configured to communicate with management dashboard 260 so as to forward to management dashboard 260 a copy of communication items between user 280 and bot server 252 (e.g., various chatbots executing on bot server 252). In some embodiments, bot server 252 is configured to communicate with management dashboard 260 to allow agent 290 to perform various tasks related to creating and managing chatbots, such as creating a chatbot, customizing a chatbot, loading a chatbot, deploying a chatbot, and delete a chatbot, etc. Bot server 252 can deploy a chatbot into a user-interactive platform, such as webpages, intranet, widgets, messaging applications, social media applications, and the like. In some embodiments, chatbots are created and managed using various toolkits, such as Microsoft Bot Framework, BotKit, Facebook Messenger Platform, API.ai, Telegram Bot, and the like. In some embodiments, bot server 252 is configured to retrieve from one or more chatbotinfo databases 253 to load and/or deploy one or more chatbots (e.g., template chatbots) to carry out the workflow associated with the service requested by user 280. In some embodiments, a bot generator 254 can be used to run one or more scripts (e.g., master Java scripts) to create chatbots from scratch, or customize chatbots loaded from chatbotinfo database 253. More details are described with reference to FIG. 4F below. In some embodiments, bot server 252 is also configured to interact with a plurality of third party services 263 in connection to delivering requested services (e.g., execute steps of a workflow) to user 280.

In some embodiments, bot server 252 is implemented on an Amazon Elastic Cloud (EC2) framework. In some embodiments, bot server 252 is configured to provide one or more of the following functionalities: a load balancer (e.g., using Nginx), a cache (e.g., using Memcached), a web server (e.g., Apache Tomcat server), a Node.JS engine, a Facebook React library, and a database storing pairs of key-value (e.g., using Redis).

In some embodiments, agent 290b need to access privacy sensitive data such as electronic medical records 256 (EMR) of user 280 in order to provide the requested service thereto. Clinician agent 290b is usually pre-authorized for access to EMR systems, or is able to request for access or qualified access to EMR systems. As used herein, clinician agent 290b may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like.

In some embodiments, healthcare facilities such as hospitals or clinics have EMR systems that store EMRs of patients, including clinical trial participants. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

In some embodiments, system 250 includes a HIPAA data store 255, which is configured to interface chatbotinfo 253, EMR 256, payment form and HIPAA compliant survey module 257, and rule engine 259 in communication with analytics stores 267.

In some embodiments, HIPAA data store 255 is configured to store all or a portion of HIPAA-sensitive communication and data that has been transacted via system 250. For example, HIPAA data store 255 can be used to hold protected health information (PHI) such as information obtained via payment forms in connection of user 280 paying for health care services or prescribed medication at system 250, and/or data obtained via HIPAA compliant surveys collected from user 280 by payment form and HIPAA compliant survey module 257 of system 250. In some embodiments, HIPAA data store 255 is configured to update, modify, or synchronize its data with the data of EMR 256. HIPAA data store 255 as well as the components it interfaces with (e.g., components that make use of the data of HIPAA data store 255, for example, rule engine 259, analytics store 267, WPC (whole person care) survey and analytics module 258. HIPAA data store 255 and EMR 256 are configured with security safeguard measures including, for example and without limitations, administrative safeguards, physical safeguards, and technical safeguards. In some embodiments, technical safeguards are configured to implement access controls, audit control, and integrity controls.

In some embodiments, bot server 252 is configured to interface with a plurality of services 263 in order to carry out the steps of a workflow assigned to user 280 in connection to delivering the requested service. Services 263 can include, for example and without limitations, an AI service (e.g., an artificial entity under the name "Sara") 263a, a video chat service 263b, a natural language processing (NLP) service 263c, payment service 263d, prescription service (Rx) 263e, Jiseki member and services API 263f, and a calendar service 263n. In some embodiments, services 263 are provided by third party service providers. For example, AI service can be enabled by X2.ai and serviced by a X2 conversation engine 262, which provides patients with access to affordable and yet quality mental healthcare using psychological artificial intelligence; Wit.ai can be used to provide NLP services; Square can be used to provide payment services, GoGoMeds can be used to provide prescription services; and Acuity can be used to provide calendar based appointment services, etc.

In some embodiments, services 263 can be implemented, assembled, or customized at system 250. For example, Jiseki member and service APIs can be implemented and/or customized using services provided from a plurality of third party providers 264 including, for example and without limitations, credit card service 264a (e.g., PDS e-cash card service), dental service 264b (e.g., Bento dental service), and payment service 264n (e.g., Stripe credit card service). For another example, Stripe credit card service 264n can be aggregated with calendar service 263n to streamline the steps required in a workflow that requires both an appointment date selection and a pre-payment for the appointment.

Again, it should be appreciated that one or more of the illustrative components/modules in FIG. 2B may include other components, sub-components, modules, sub-modules, and device commonly found in a communication/computing system, which are not discussed above with reference to Jiseki system and not discussed herein for clarity of the description. Additionally, in some embodiments, one or more of the illustrative components/modules can form a portion of another component/module and/or one or more of the illustrative components/modules can be independent of one another.

Figure 3A:
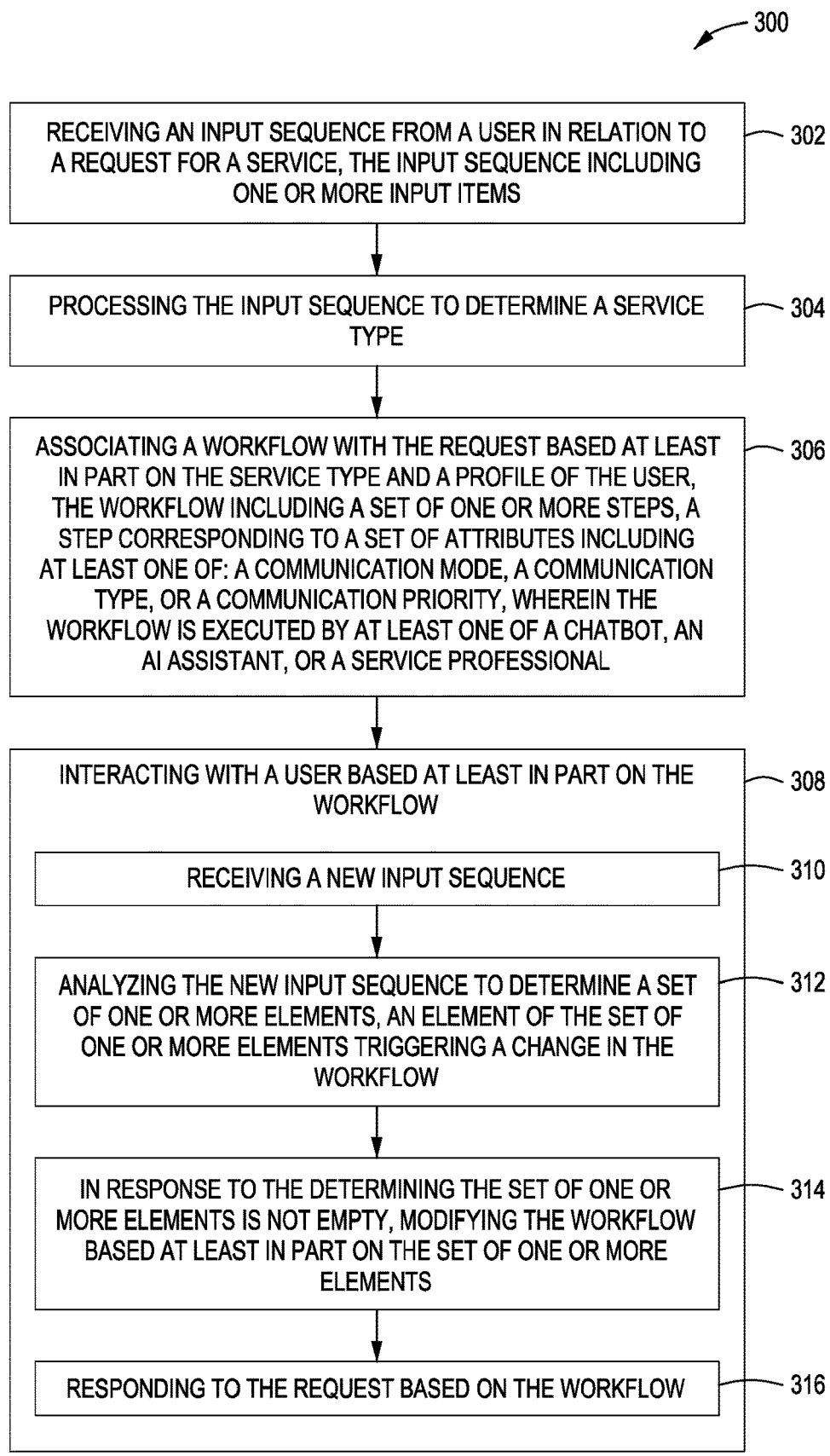
FIGS. 3A-C are flow charts of example processes for AI assisted service provisioning and modification for delivering message-based services, in accordance with one or more embodiments of the present disclosure.
Figure 3B:
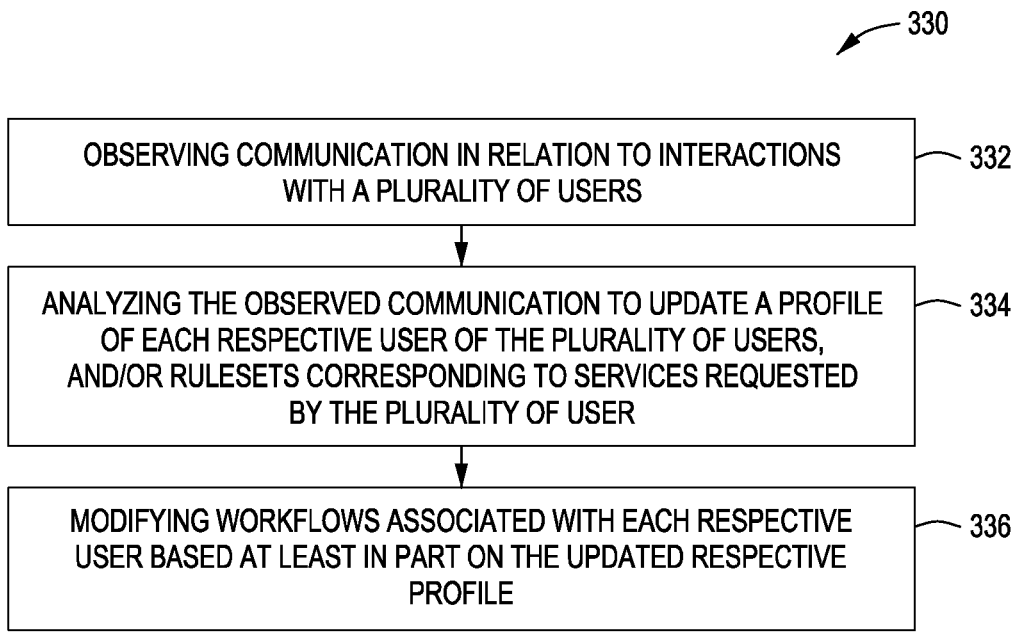
Figure 3C:
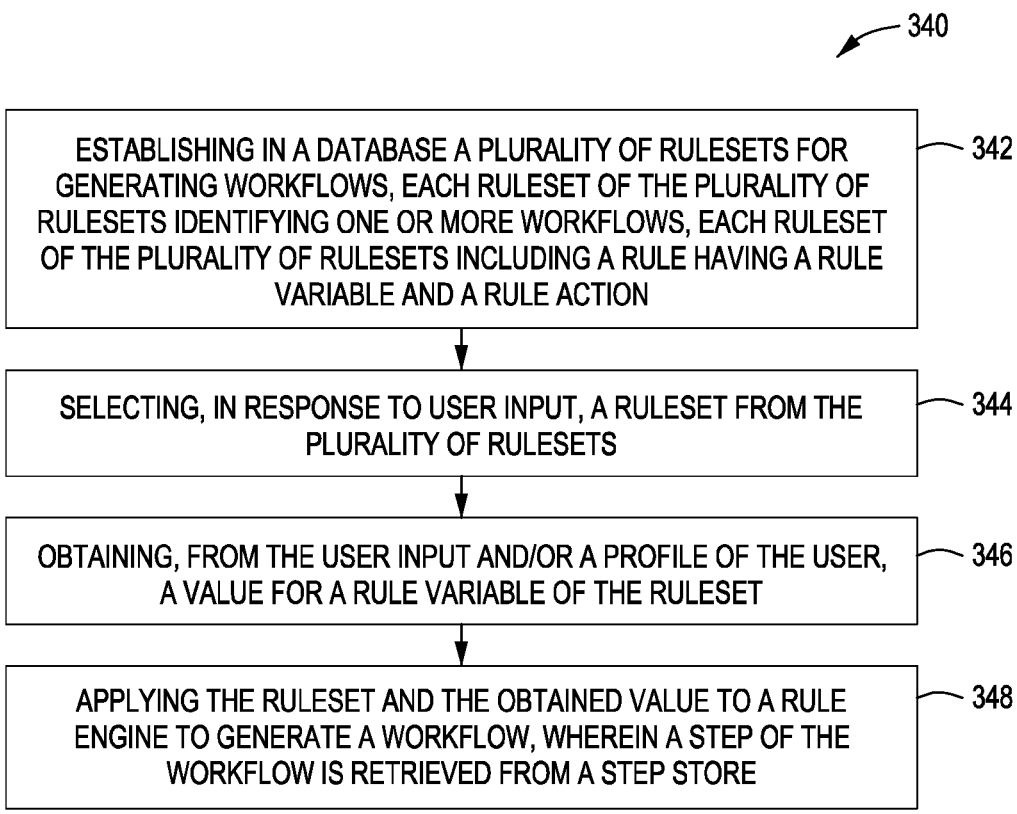

FIG. 3A-C illustrate flow charts of example processes for AI assisted service provisioning and modification for delivering message-based services in accordance with an embodiment of the present disclosure. Processes 300, 330, and 340 can be implemented by, for example and without limitations, platform 106 of FIGS. 1A-C, cloud 108 of FIG. 1C, platform 206 of FIG. 2A, system 250 of FIG. 2B, and processor 802 of FIG. 8. The following illustrate processes 300, 330, and 340 from the perspective of platform 206 of FIG. 2A.

Process 300 starts at 302, where an input sequence is received from a user in relation to a request for a service. In some embodiments, listener 221 of platform 206 receives the input sequence from the user. In some embodiments, the input sequence includes one or more input items. For example, an input item can include one or more tokens (e.g., hashtags) recognizable at platform 206. At 302, the input sequence is processed to determine a service type. In some embodiments, router 224 processes the input sequence to determine whether the one or more input items correspond to pre-defined tokens representing their respective service type. In some embodiments, a voice based input sequence is converted to text using speech-to-text techniques. In some embodiments, router 224 further utilizes a user profile information to determine a service level accessible for the user, after matching the one or more input items to recognizable tokens.

At 306, the user request is associated with a workflow based at least in part on the service type and a profile of the user, the workflow being executed by at least one of: a chatbot, an AI assistant, or a service professional. The workflow includes a set of one or more steps, a step of the set of one or more steps corresponds to a set of attributes including at least one of: a communication mode, a communication type, or a communication priority. In some embodiments, workflow manager 233 retrieves from ruleset store 234 one or more rulesets according to the service type, and applies the one or more rulesets, and/or data in the profile of the user to rule engine 218 to generate a workflow.

At 308, the user is interacted with based at least in part on the workflow. In some embodiments, step 308 further comprise steps 310 through 316. At 310, a new input sequence is received at platform 206. At 312, the new input sequence is analyzed to determine a set of one or more elements, an element of the set of one or more elements triggering a change in the workflow. In some embodiments, classify and summarize sub-module 231 analyzes the new input sequence to determine whether there is any element that triggers a change in the workflow by classifying, summarizing, ranking the new input sequence from the user. In some embodiments, an element corresponds an intent or goal of the user. In some embodiments, an element corresponds to the values of the variables utilized in rule conditions of the rules in the rulesets that are used to determine the workflow.

At 314, in response to the determining that the set of one or more element is not empty, the workflow is modified based at least in part on the set of one or more elements. In some embodiments, workflow manager 233 modifies the workflow based on the determined set of one or more elements. In some embodiments, independent from whether the set of one or more elements is empty, workflow manager 233 modifies the workflow based on the profile of the user and/or updates to the profile of the user, using the profile data as one or more rule variable values for evaluating the rulesets to generate the workflow. In some embodiments, the updates to the profile trigger changes in the evaluation, and/or selection of the rulesets that are used to determine the workflow. In some embodiments, workflow manager 233 modifies the workflow based on previous communication with the user in relation to services of the service type, and/or services of types other than the service type. In some embodiments, workflow manager 233 modifies the workflow based on communication with other users on platform 206, in relation to services of the service type, and/or services of types other than the service type. At 316, the request is responded to based on the workflow.

FIG. 3B illustrates a flow chart of an example process for AI assisted service provisioning and modification for delivering message-based services in accordance with an embodiment of the present disclosure. Process 330 starts at 332, where communication in relation to interactions with a plurality of users is observed. In some embodiments, platform 206 records the communication (including data related to the communication) with all the user in response store 237. In some embodiments, platform 206 records pairs of user input and one or more responses in response store 237. In some embodiments, the communication includes surveys proactively transmitted to the user and relies back to platform 206. At 334, the observed communication is analyzed to update a profile for each respective user of the plurality of users, and/or rulesets corresponding to services requested by the plurality of users. In some embodiments, response store 237 and ruleset store 234 includes its respective intelligence with regard to analyzing the communication. In some embodiments, response store 237 and ruleset store 234 leverage on the functionalities of classification and summarize sub-module 231, and/or workflow manager 233 to analyze and update profiles and rulesets. In some embodiments, AI models are utilized to update the profile of each perspective user, and/or the rulesets based on which services are provided. In some embodiment, the AI models are also trained and/or retrained in order to perform the updates. At 336, workflows associated with each respective user is modified based at least in part on the updated perspective user profile, and/or corresponding one or more rulesets. In some embodiments, workflow manager 233 reapplies the data in the profile of a user to the ruleset which is used to generated the workflow. In some embodiments, workflow manager 233 reapplies the data in the profile of a user to the modified ruleset that is used to generate the workflow.

FIG. 3C illustrates a flow chart of an example process for AI assisted service provisioning and modification for delivering message-based services in accordance with an embodiment of the present disclosure. Process 340 starts at 342, where a plurality of rulesets are established in a database for generating workflows, each ruleset of the plurality of rulesets identifying one or more workflow, each rule of a ruleset having a rule variable and a rule action. In some embodiments, Jiseki engineering creates rulesets corresponding to respective service types, surveys, and the like using established protocols, best practice, guidelines, surveys, etc. and stores the ruleset in ruleset store 234. At 344, a ruleset is selected from the plurality of rulesets in response to user input. In some embodiments, workflow manager 233 selects one or more rulesets based the service type determined using the user input. In some embodiments, workflow manager 233 selects one or more rulesets based on the analysis results of the user input, such as answers to surveys and/or questionnaires. In some embodiments, workflow manager 233 selects a default ruleset using the WPC scoring in addition to the afore-described selection. At 346, values are obtained for the rule variables from user input, and/or a profile of the user. In some embodiments, workflow manager 233 retrieves the correspondent data in the profile of the user as variable values. In some embodiments, workflow manager 233 obtains variable values by analyzing the user input, such as answers to surveys and/or questionnaires. At 348, the ruleset(s) and the obtained values are applied to a rule engine (e.g., rule engine 218) to generate a workflow, wherein a step of the workflow is retrieved from a step store (e.g., response store 237).

FIG. 4A illustrates a portion of a graphical representation of an example user interface of internal UI 214 of FIG. 2A in accordance with an embodiment of the present disclosure. In some embodiments, a professional (e.g., doctors, counselors, therapists, personal financial advisors, etc.) and/or a platform administrator is provided with an internal user interface 214 (e.g., professional GUI) at platform 206. In some embodiments, workflows are started with a bot (e.g., workflow are started in a Chatbot window) for a user who has interacted with platform 206 beforehand (e.g., received message-based services at platform 206, registered with platform 206, etc.), or initiated at the user's request, or by professionals after they've learned more about the user. As shown herein, in some embodiments, via a chatbot provisioning window 400, a platform administrator/professional provisions chatbots to service conversation requests. For example, the professional can specify on which topic (e.g., health related questions, finance related questions) a chatbot is to be provisioned by interacting with a topic picker 402, how often (e.g., on a daily basis, weekly basis) the chatbot is to be provisioned by interacting with a frequency picker 404, and how many users the chatbot is tasked for interaction (e.g., initiate Bot for 1 user, or for 2 users) by interacting with a quantity picker 406.

Figure 4C:
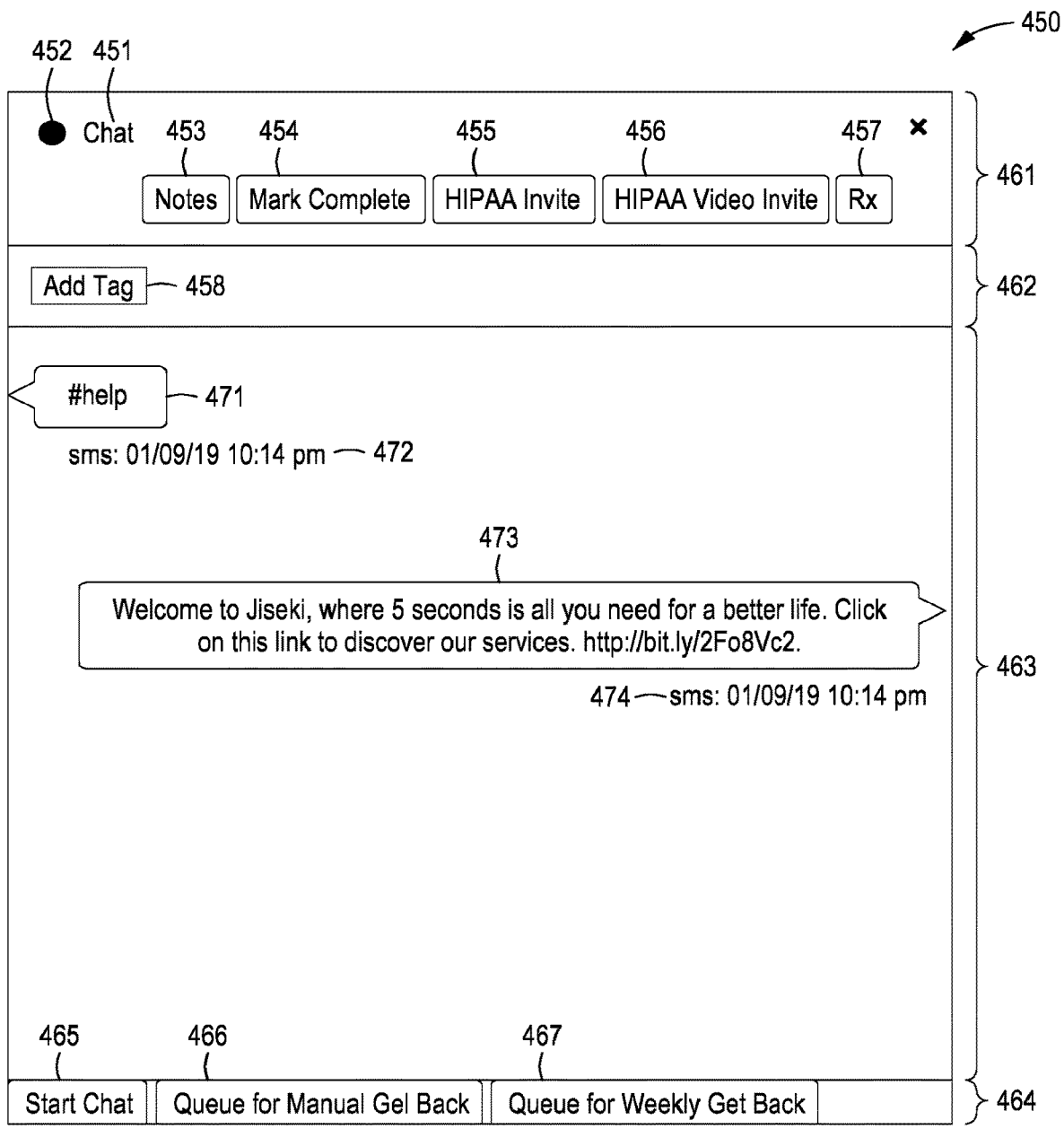

FIG. 4B illustrates a portion of a graphical representation of another example user interface of internal UI 214 of FIG. 2A in accordance with an embodiment of the present disclosure. In some embodiments, a professional and/or a platform administrator is provided with an internal user interface 214 (e.g., professional GUI) at platform 206. As a portion of the display of a console dashboard 420 illustrates herein, a professional (e.g., an agent) can access an overview summary of all the ongoing, completed and pending requests/conversations at platform 206. In some embodiments, dashboard 420 displays the conservations with the following categories of information: flags (412), organization (413), birth date (414), birth year (415), timestamp (416), channel (417), agent number (418), agent name (419), status of being assigned or not (421), tags (422), and buttons to start chats (423). In this example, dashboard 420 displays a plurality of snippet rows 431-436 for a plurality of users accessing a platform 206. As illustrated herein, dashboard 420 shows relevant histories for all or a filtered subset of the users, including conversations with automation conducted during the course of delivering services to the users. In some embodiments, for different professionals, dashboard 420 displays the portions of the user communication history that is pertinent to the particular professional, e.g., relevant as the context of a conversation stored with each response indicates. For example, a financial advisor would only see the part of a user's conversation history pertaining to financial issues. In some embodiments, metadata associated with each conversation regardless of the service type or context is displayed at dashboard 420 to all types of professionals. For example, a financial advisor cannot view the content of the chat between a user and a medical agent, but can view, for example, when and for how long the user communicated with the medical agent. If the medical agent has shared a note regarding the chat with the user for the financial advisor (or all other agents servicing the user), the financial advisor can view that note as well. In some embodiments, dashboard 420 allows searching for one or more particular users, user communication history, etc. using, for example, an identifier (such as a name or phone number of the one or more users). In some embodiments, upon clicking on a "Chat" button displayed at each of rows 431-436, the professional traverses to a conversation window (e.g., window 450 of FIG. 4C), at which the professional may choose to communicate with the user manually and send a message immediately, or select a communication mode (such as video chat), and/or specify a communication type, such as sending a conversation to a bot or an AI assistant, with various buttons and menu choices (details are described with reference to FIG. 4C).

In some embodiments, dashboard 420 displays a status for pending service requests as "unassigned," or the names of the professional, chatbot, or AI assistant the conservation has been assigned to. In some embodiments, dashboard 420 also includes a UI element (e.g., link) to allow reporting on, including, for example, information such as the number of conversations, user administration, user statistics, professional statistics, bots/AI assistant statistics, etc. In some embodiments, dashboard 420 further includes one or more UI elements to allow defining rules as well.

FIG. 4C illustrates a portion of a graphical representation of another example user interface of internal UI 214 of FIG. 2A in accordance with an embodiment of the present disclosure. In some embodiments, a service professional (e.g., doctors, counselors, therapists, personal financial advisors, etc.) and/or a platform administrator is provided with an internal user interface 214 (e.g., professional UI) at platform 206. In some embodiments, a conversation window 450 is configured as part of the afore-described professional UI 214. In some embodiments, conversation window 450 includes an indicator 452 to reflect that the user has already been engaged with by a chatbot or other automation. Conversation window 450 also includes one or more buttons on a top panel 461. The set of one or more buttons include a "Notes" button 453, a "Mark Complete" button 454, a "HIPAA Invite" button 455, a "HIPAA Video Invite" button 456, and a "Rx" button 457. Conversation window 450 also includes a "Add Tag" button 458 in a mid-panel 462, a message displaying area in a lower panel 463, as well as a set of tabs in a bottom panel 464. The set of tabs includes a "Start Chat" tab 465, "Queue for Manual Get Back" tab 466, and "Queue for Weekly Get Back" tab 467.

In some embodiments, a professional (e.g., an agent) can click the "Start Chat" tab 465 to begin a message-based session with a user, in response to receiving a user input. If the user has already been serviced by a chatbot, the professional is then taking over the conversation. As illustrated herein, in response to the user sending an input 471 (e.g., a SMS message of "#help") having a respective timestamp 472, the professional enters a response 473, which also has a respective timestamp 474. Further, the service professional can click on "Notes" button 453 to add notes about his or her interaction with the user; click on the "Mark Complete" button 454 to mark conversation as complete to indicate that this particular service request (e.g., issue-driven interaction) has been fulfilled; click on the "HIPAA Invite" button 455 to generate a special link for being texted to the user to invite him or her to a secure web chat; click on the "HIPAA Video Invite" 456 button to generate a special link for being texted to the user to invite him or her to a secure video web chat; click on the "Rx" button 457 (by authorized professionals only) to initiate the process of writing a prescription; click on the "Add Tag" button 458 to tag the request for later reference. For instance, after finding out more about what kind of help the user is seeking, the professional can tag the request with, for example, #plan, #sara, #talk, etc. In some embodiments, tags are similar to flags, which are described with more detail below.

Moreover, in response to receiving a user input (e.g., #help), and/or at any point during the conversation with the user, the professional can click on "Queue for Manual Get Back" tab 466 to send/continue the service request to special queues to follow-up manually; or click on "Queue for Weekly Get Back" tab 467 to send/continue the service request to special queues to follow-up on a weekly basis, either by the professional or by an automation.

In some embodiments, users can flexibly interact with the platform via input items (e.g., tokens, hashtags, keywords) to activate particular services. The platform is configured to profile the users to provision initiation of automated conversations, manual conversations, and the combination thereof based on the information available at the platform. In some embodiments, as described above, the platform is configured to conduct a whole person care survey (WPC survey) at the time a new user subscribing to the platform for services, and stores the survey result information in a profile store (e.g., profile store 238 of FIG. 2A). The survey result information includes data such as user names, gender, birth date, address, phone number, email account, medical history, financial background, triage scoring, etc. The platform is also configured to collect data pertaining to the user, such as access patterns, content of the previously/on-going/scheduled conversation delivering same and/or different types of services. A professional/conversation GUI includes elements to accomplish this (as illustrated in FIGS. 4A-G) manually, or with suggestions from the platform. Further, an internal data store (e.g., response store 237, ruleset store 234 of FIG. 2A) and workflow manager 233 (e.g., using rule engine 218 of FIG. 2A) are connected through programmed rulesets to accomplish the same automatically. In some embodiments, the rulesets are programmed by experts or learned via AI models.

Figure 4D:
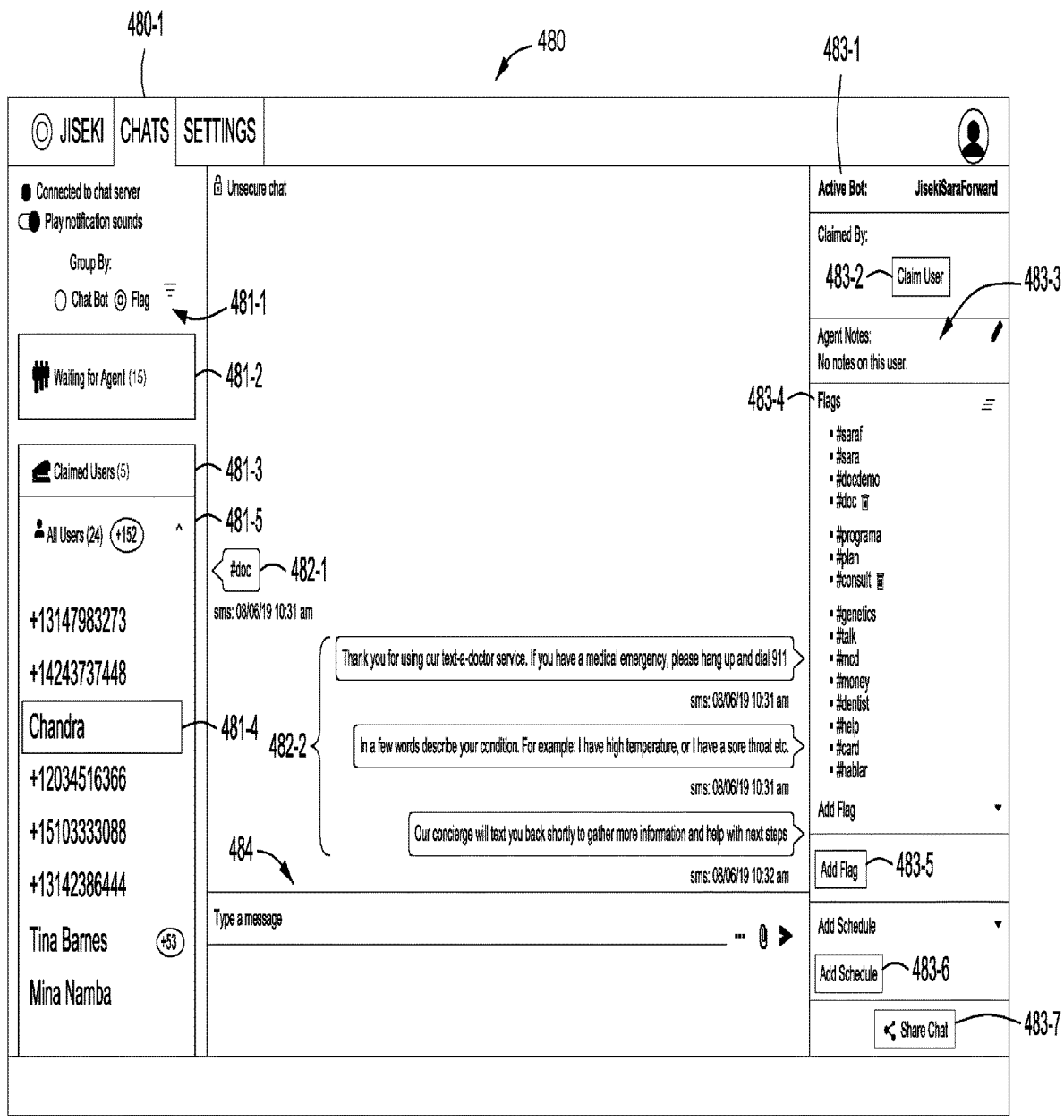

FIG. 4D illustrates a portion of a graphical representation of yet another example user interface of internal UI 214 of FIG. 2A in accordance with an embodiment of the present disclosure. In some embodiments, UI 214 includes a dashboard window 480, which is configured with one or more tabs (e.g., HOME, CHATBOTS, CHATS, ANALYTICS, SETTINGS) on a top panel. The number of tabs on dashboard 480 can be configured differently depending on the roles of the agent at dashboard 480. As shown herein, dashboard 480 is displayed with tabs "CHATS" and "SETTINGS", with the tab "CHATS" 480-1 as the selected tab. On the left hand panel, an status indicator is shown to confirm dashboard 480 as being connected to a chat server and therefore having access to the messages associated therewith. A notification indicator is also shown to reflect the setting of whether dashboard 480 is configured to play notification sounds upon various alerts, or the like. An agent (e.g., professional) interacting with dashboard 480 can toggle the notification indicator to switch from the setting of not playing notification sounds to the setting of playing notification sounds, or vice versa. As shown herein, the agent chooses to let dashboard 480 play the notification sound upon notifications. Further, the agent can click on either radio button of a radio button group 481-1 to select to group all the communication accessible at dashboard 480 (e.g., all the messages accessible at dashboard 480) either based on whether a chatbot has already been provisioned to engage the users, or based on the one or more flags assigned to each user's request(s). More details about the usage of flags at dashboard 480 are described below with reference to the right hand panel of dashboard 480.

Also at the left hand panel, dashboard 480 is configured to present multiple summaries with respect to the processing of the requests received from the users. For example, a "Waiting for Agent" summary 481-2 shows in its parenthesis how many users communicating via the chat servers associated with dashboard 480 are waiting to be assigned to an agent. As shown herein, a count of fifteen (15) user are waiting and therefore, these requesting users have not been assigned to a respective agent. The count is updated in real time according to how many new user requests are received at dashboard 480, as well as how many existent users' requests have been assigned to agents. Additionally, a "Claimed Users" summary 481-3 shows in its parenthesis how many users have been claimed (e.g., assigned to) the agent interacting with dashboard 480. In some embodiments, the agent, by claiming a user from a waiting list queued up at dashboard 480, starts engaging with the user to handle the user's service request. This way, the count of the total number of users waiting for an agent decrease by one; and the count of the claimed users associated with the agent increase by one. On the other hand, once the agent is done fulfilling the user's request, the agent releases the claim upon the user so that the count of the claimed user associated with the agent decrease by one. As shown herein, presently the count of the users claimed by the agent is five (5). Similarly, the count of the claimed users is updated according to how many new users the agent has claimed to handle, as well as how many existent users the agent has released.

Still at the left panel of dashboard 480, an "All User" panel 481-5 is configured to display a summary of a count of total users in its parenthesis. As shown herein, a total of 24 entries of users are displayed in panel 481-5. In some embodiments, the count is computed based on how many new users have started communication, how many users are in the middle of being serviced, and how many users have completed communication at platform 206. Underneath the summary, a list of all the users counted in the summary are displayed in, for example, a scrollable sub-panel. In some embodiments, a user is represented by a phone number associated therewith, the user's name, or the like. The agent can click upon any user in the list to access the communication channel in the middle panel. As shown herein, user "Chandra" 481-4 is selected and consequently, the middle panel displays a first message "#doc" 482-1 transmitted from user 481-4, as well as a series of messages 482-2 generated by a chatbot (e.g., JisekiSaraForward) in response to receiving first message 482-1. In some embodiments, when the agent starts to enter a response in a message box 484 and/or clicks on an icon to cause the entered response to be transmitted to user 481-4, dashboard 480 registers the action(s) as the agent claiming user 481-4 in a manner alternative and additionally to clicking on a "Claim User" button 483-2 at the right hand panel. In some embodiments, dashboard 480 prompts the agent with a pop-up window (not shown) to confirm whether the agent indeed intends to terminate the chatbot (e.g., the active bot JisekiSaraForward) which has been conversing with user 481-4. At this point, the agent can either choose to confirm (e.g., by clicking on a "Yes" button), or to cancel (e.g., by clicking on a "No" button) the taking over action. In the first case, the agent claims selected user 481-4 to start handling user 481-4's request manually. In the second case, the agent decides not to claim user 481-4 anyway, thereby reverting back the effect of the agent entering a response and sending of the entered response. In some embodiments, dashboard 480 further prompts the agent to login under a role other than the current one associated with the logging-in account of the agent. For example, dashboard 480 can prompt the agent to log in as an administrator. In some embodiments, upon being prompted, the agent can switch the logging-in account to a super-agent or agent manager role so that the agent can further perform other actions, such as assigning user 481-4 to other agents under his/her management.

Now referring to the right hand panel of dashboard 480, at the top, an "Active Bot" section 483-1 is displayed to indicate that a chatbot of the type of JisekiSaraForward is presently assigned to engage user 481-4 upon the receipt of an initial request (e.g., #doc). Upon clicking on the "Claim User" button 483-2, the agent takes over interacting with user 481-4. Similarly, in some embodiments, dashboard 480 prompts the agent with a pop-up window (not shown) to confirm whether the agent indeed intends to terminate the chatbot (e.g., the active bot JisekiSaraForward) conversing with selected user 481-4. As the interactions are substantially similar to the above-described with reference to the middle panel, the details are not repeated herein for the purpose of simplicity.

After claiming user 481-4, in addition to allowing the agent to start communicating (e.g., text, video, HIPAA compliant communication, sending attachment links) with selected user 481-4, dashboard 480 also allows the agent to perform a variety of actions in relation to handling the service request from user 481-4. For example, the agent can record notes regarding user 481-4 by entering information into a note area 483-3. The agent can also view a list of all the flags that have been associated with the service request of user 481-4 in a flag area 483-4. Further, the agent can assign new flag(s) to the instant service request by clicking on a "Add Flag" button 483-5. Upon the agent associating a new flag with the request, dashboard 480 updates the list entries in flag area 483-4, as well as update the list/count of the users grouped by that newly added flag so as to populate the left hand panel with the current information.

Furthermore, dashboard 480 allows the agent to initiate and/or terminate collaboration with other chatbots, AI assistants, and agents during the course of handling the instant service request from user 481-4. For example, the agent can click on a "Add Schedule" button 483-6 to schedule a chatbot to service user 481-4 by navigating to a CHATBOT tab of dashboard 480, the details of which is illustrated with reference to FIG. 4F below. The agent can also share the communication in response to the instant service request by clicking on a "Share Chat" button 483-7. Upon the agent choosing to share the instant chat, dashboard 480 further provides the agent with GUI elements (not shown) to select/specify which other agent(s) to share the chat with, how the instant chat is to be shared, and the like. In some embodiments, the two-party communication between user 481-4 and the agent becomes a group communication with additional agent(s) with whom the chat has been shared.

Figure 4E:
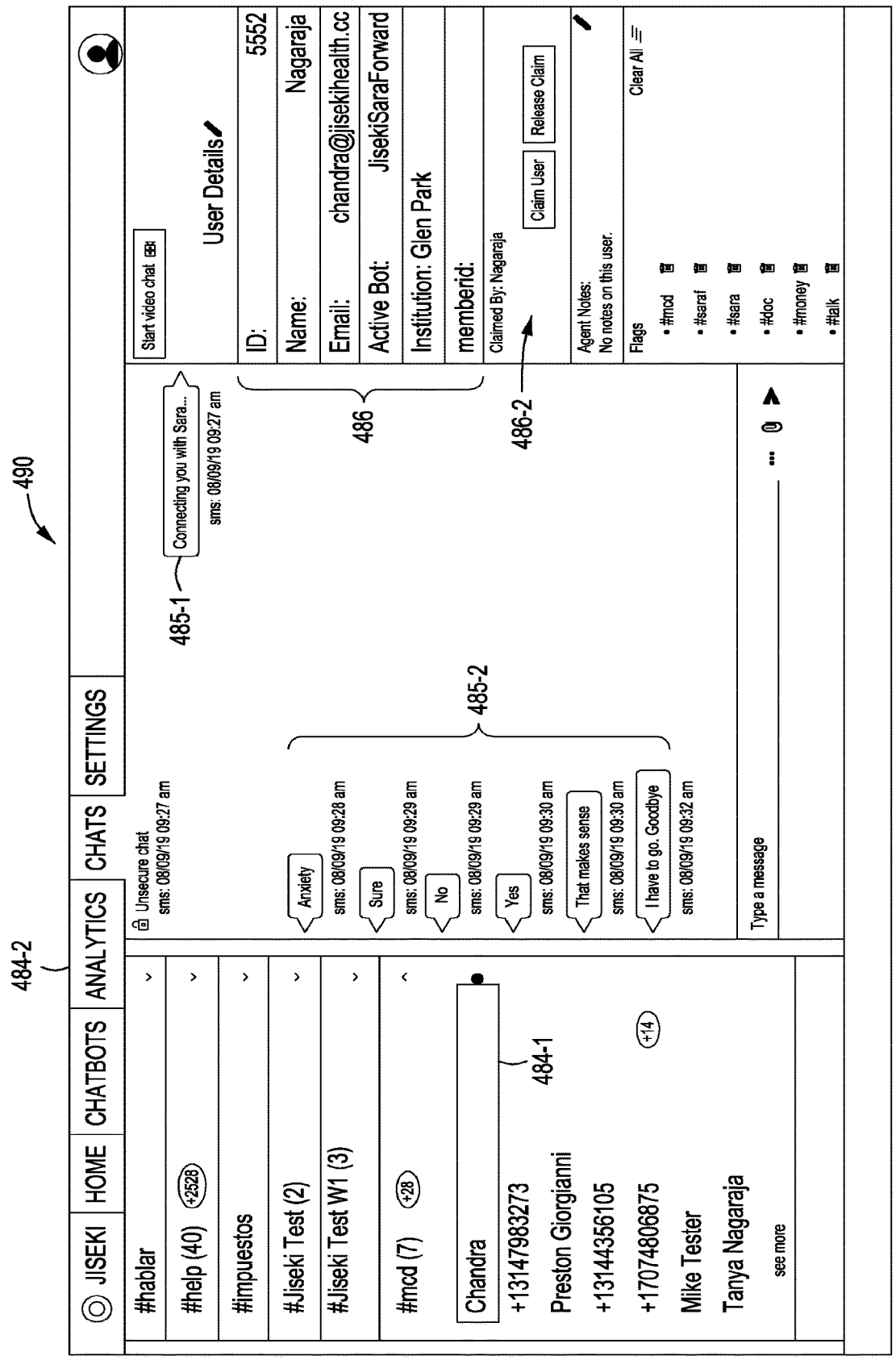

FIG. 4E illustrates a portion of a graphical representation of another example user interface of internal UI 214 of FIG. 2A in accordance with an embodiment of the present disclosure. In some embodiments, GUI 214 includes a dashboard window 490, which is configured with a group of tabs of "HOME," "CHATBOTS," "CHATS," "ANALYTICS," and "SETTINGS." As shown herein, dashboard 490 is displayed with tab "CHATS" 484-2 as the active tab. At the left hand panel, dashboard 490 displays a portion of an "All Users" panel, which lists all the users grouped under the one or more flags, e.g., #hablar, #help, #impuestos, #mcd, etc., associated with their respective requests. As shown herein, the agent has selected the group flagged with "#mcd" to expand in a dropdown list to show all the users having requests flagged with #mcd (e.g., handled by one or more professionals associated with the MCD organization). Similarly, the requesting users are represented by their names, phone numbers, or the like. Here, user "Chandra" 484-1 is selected by the agent, and the communication occurred so far is displayed at the middle panel.

At the middle panel of dashboard 490, a portion of the communicated messages are displayed to the agent for viewing. For example, in response to the request (not shown) from user 484-1, a chatbot of the type "JisekiSaraForward" has responded with a message 485-1; and user 484-1 has further replied with a series of new input messages 485-2.

At the right hand panel of dashboard 490, a portion of the right hand panel is displayed to show some details of user 484-1 in an area of "User Details" 486. In some embodiments, user details 486 displays information such as the user ID, name, email address registered, active bot assigned thereto, institution affiliation, member ID, and the like. At this point, user 484-1 is serviced by a chatbot of the type "JisekiSaraForward" and therefore the active bot assigned entry indicates "JisekiSaraForward." Additionally, user 484-1 has also been previously claimed by the agent (e.g., agent Nagaraj a, and the previous communication is not shown in this partial interface display), and the agent can click on "Release Claim" button in the "Claim by" area 486-2 to stop handling the request of user 484-1. In other words, the agent can remove user 484-1 from the list of users queuing to be serviced by the agent.

Figure 4F:
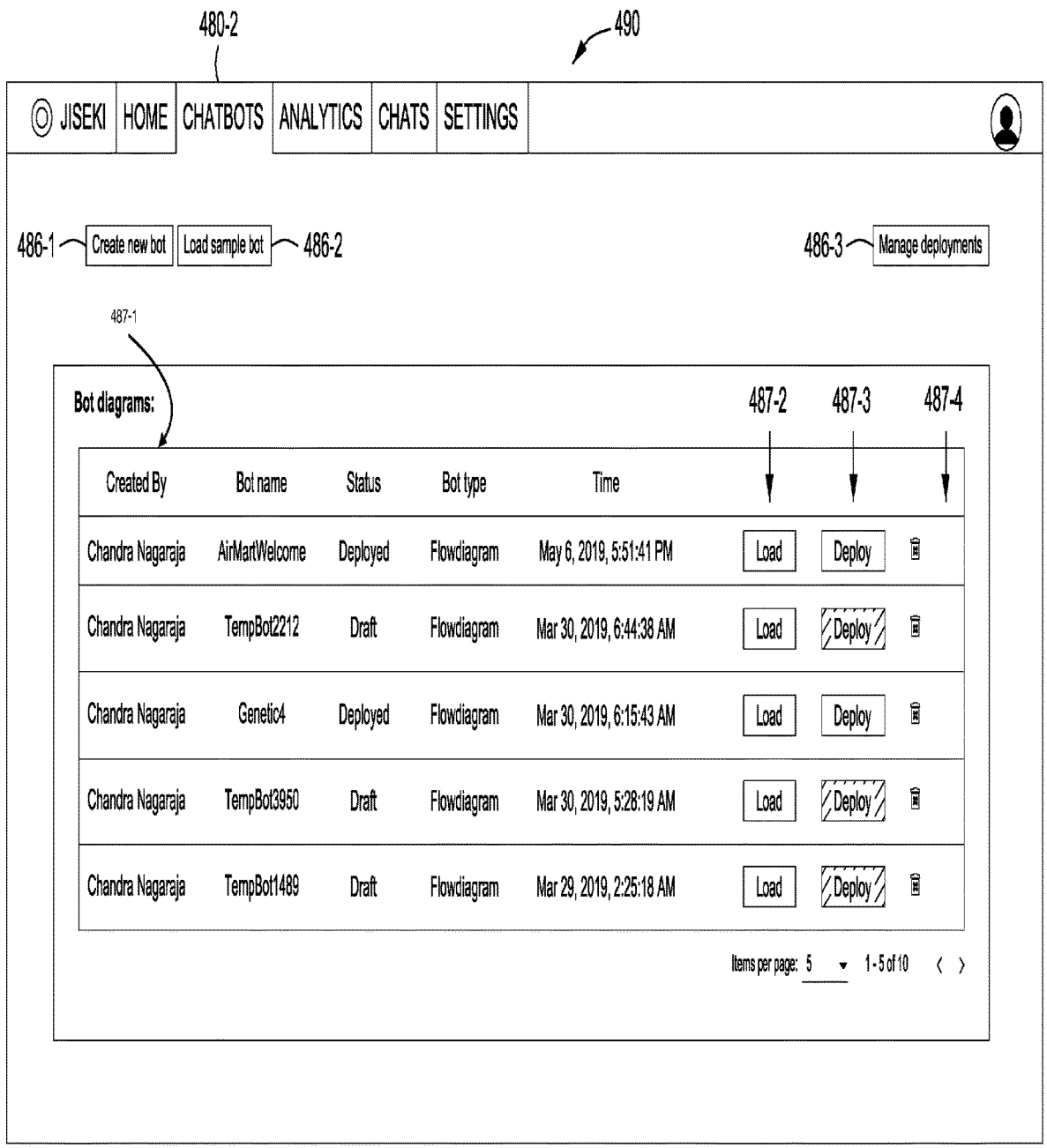

FIG. 4F illustrates a portion of a graphical representation of another example user interface of internal UI 214 of FIG. 2A in accordance with an embodiment of the present disclosure. In some embodiments, UI 214 includes a dashboard window 490, which is configured with a group of tabs of "HOME," "CHATBOTS," "CHATS," "ANALYTICS," and "SETTINGS." As shown herein, dashboard 490 is displayed with tab "CHATBOTS" 480-2 as the active tab. Under "CHATBOTS" tab 480-2, the agent can click on a "Create new bot" button 486-1 to create a chatbot without using any template bots, or click on a "Load sample bot" button 486-2 to modify an existent template bot into a new chatbot. A table of "Bot diagram" displays the information relating to all the created chatbots that can be loaded and/or deployed. In some embodiments, the information includes, for example but not limited to, who creates the bot, a bot name, a bot status, a bot type, and a time stamp associated with a bot (e.g., bot's deploy time). At column 487-1, an identification of (e.g., names of an agent, an administrator) who creates the chatbot is displayed. For each bot displayed, at column 487-2, a "Load" button is displayed to allow the agent to load the respective bot; a "Deploy" button is displayed at column 487-3 to allow the agent to deploy the respective bot; and a recycle can icon is displayed at column 487-4 to allow the agent to delete the respective bot. For some bots, both the load button and the deploy button are active for selecting (e.g., the AirMartWelcome bot at row 1); while for some other bots (e.g., tempbot212 at row2), only the load button is available while the deploy button is unavailable (indicated with the hatching lines).

FIG. 4G illustrates a portion of a graphical representation of another example user interface of internal UI 214 of FIG. 2A in accordance with an embodiment of the present disclosure. In some embodiments, UI 214 includes a dashboard window 490, which is configured with a group of tabs of "HOME," "CHATBOTS," "CHATS," "ANALYTICS," and "SETTINGS." As shown herein, dashboard 490 is displayed with tab "SETTINGS" 490-1 as the active tab. Under "SETTINGS" tab 490-1, the agent can configure a variety of settings for dashboard 490 using the links in the left hand panel. For example, by clicking on "Agents" link 490-2, the agent can access an agent table to view, search for, add, or remove agents. For example, by clicking on "Add Agent" button 490-3, the agent can add to the agent group a new member by specifying the information such as the agent name, and the role assigned to the agent.

Figure 5:
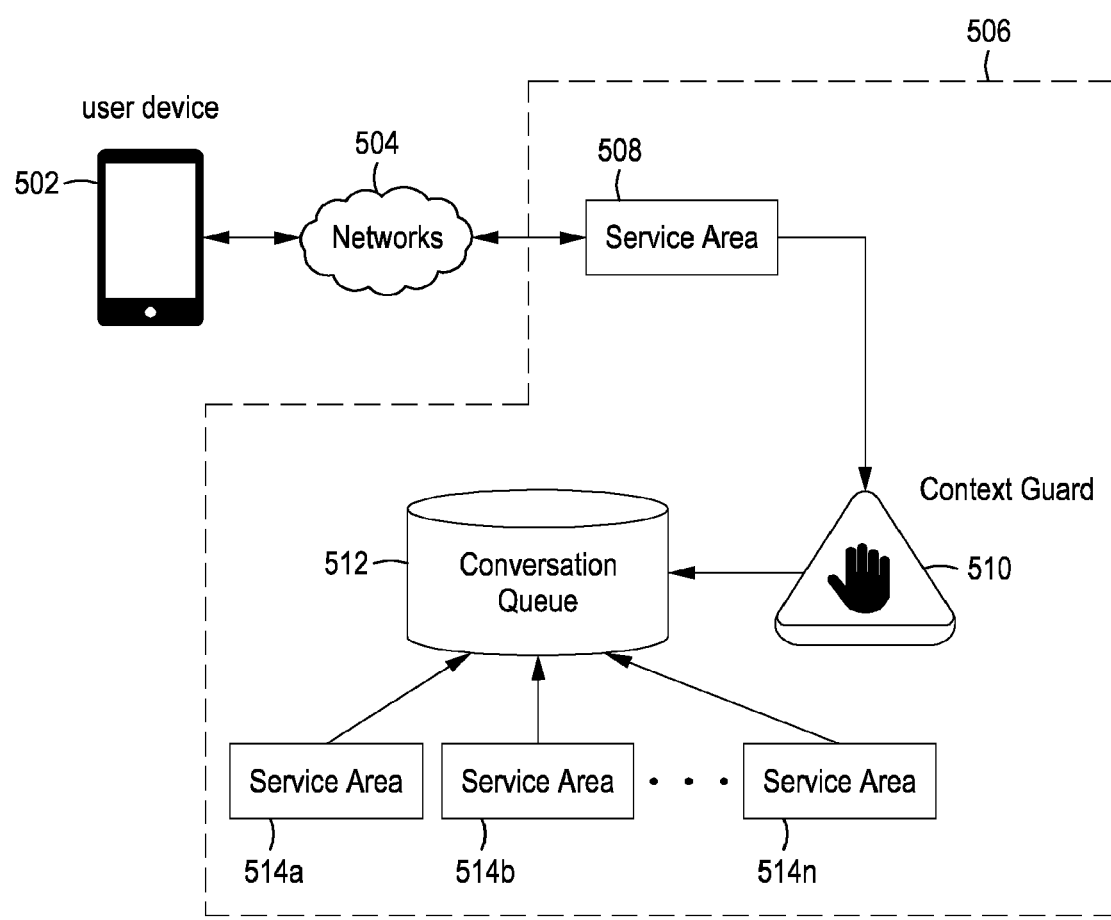
FIG. 5 is a simplified block diagram of an example context guard used in connection with AI assisted service provisioning and modification for delivering message-based services, in accordance with one or more embodiments of the present disclosure.

FIG. 5 illustrate a block diagram of an example context guard used in connection with AI assisted service provisioning and modification for delivering message-based services, in accordance with an embodiment of the present disclosure. As shown herein, a user (not shown) at a user device 502 communicates with a platform 506 via a network 504 in order to request, and/or receive services provided at platform 506. In some embodiments, client 502 can be implemented by, for example and without limitations, client 102 of FIGS. 1A-C; and network 504 can be implemented by, for example and without limitations, network 104 of FIGS. 1A-C. Platform 506 can be a part of one or more servers 106. In some embodiments, tasks performed by platform 506 can be performed by a plurality of servers 106, e.g., being allocated amongst the plurality of servers by an application, service, process, daemon, routine, executable logic, or other task allocation techniques. In some embodiments, platform 506 can be implemented at, for example and without limitations, servers 106 of FIGS. 1A-B, and/or cloud 108 of FIG. 1C.

In some embodiments, multiple professionals communicate with (e.g., text-messaging) a same user at the same communication modality on the user's end (e.g., SMS, text-messaging application on the same device). Thus, it is important to ensure that the professionals don't clash or talk over one another. Furthermore, it is also important to ensure that the professionals don't reveal confidential and/or privileged communication to these who can access the communication from the modality of the user at platform 506, but not permitted with access to a particular portion related to a particular service. For example, under the legal rules, a medical doctor or any other professionals is not allowed to access the communication exchanged between the user and a legal professional at platform 506. On the contrary, for example, in the fields absent strict confidentiality rules, a professional (e.g., a dietitian) and another (e.g., a personal trainer) may choose to always share communication with each other when it comes to consult the user at platform 506 to deliver synergized results for the user. As a compromised way of sharing communication within respective service fields, for example, a mental health care provider may leave a note about the user and specify what other professionals (e.g., doctors, nurses, social workers, financial advisor) can access the note about the user based on confidential communication.

Platform 506 is configured with an internal signaling mechanism to achieve the above-described communication sharing. In some embodiments, the signaling is based on the service roles associated with the professional, chatbots, and AI assistants at platform 506. Essentially, when a bot, an AI assistant, or a professional starts to communicate with a user (e.g., claims a user's request), platform 506 assigns the user and that portion of the communicating a context, which is protected by a corresponding context guard 510. This way, professionals at platform 506 can only access portions of communication (e.g., chat snippets) in a manner that is dictated by the permission associated with their roles. In other words, professionals only temporarily own the control/access of the portion of the communication until the portions are released (e.g., the chat is completed, or inactive after a period of time). As shown herein, when the user engages a particular service area 508 and thereby communicating with the associated professionals, bots, or AI assistants, context guard 510 is activated and attached to service area 508 such as to prevent professionals in other service areas from entering the same conversation haphazardly. If, during the meanwhile of the user engaging platform 506 in service area 508, professionals in the other service areas 514a, 514b, ..., 514n will queue their communication into a conversation queue 512, or simply wait until they're no longer locked out from communicating with the user by context guard 510. For example, during a financial advisor consultation communication, a medical follow-up chatbot is not allowed to interject any communication in the ongoing consultation session, or view the content of the session. In some embodiments, some or all the metadata (e.g., timestamps, topics) pertaining to the conversation related to service area 508 is allowed to be accessible or visible to other professionals, chatbots, and AI assistants associated with the other service areas 514a-n. In some other embodiments, a service professional, chatbot, or AI assistant associated with service area 508 may choose to share a note related to the conversation in service area 508 to the other professionals, chatbots, AI assistants associated with the other service areas 514a-n. In some embodiments, conversation tracking sets the context guard so that additional conversation is properly assigned to that context and other contexts (including workflows operating within them) can't talk to the user until the tracking determines that the conversation is done.

In some embodiments, the ability to manage context guard allows platform 506 to not only maintain separate conversation strands, but also to ensure that information is properly shared amongst professionals, conversations are timely provisioned without interference with each other. For example, a user may text a nurse, then consult with a doctor, and talk to the nurse again. All of these are within a medical context allowing internal sharing. But if the user then messages a request for a financial advisor, the conversation context has shifted, and the financial advisor, in addition to only being able to see parts of the conversation history related to that context, will trigger a separate workflow to, for example, engage the user in a bot conversation about personal finances, or pass the user to, for example a tax lawyer. This way, the sequence of events and interactions won't affect or interfere with a separate doctor-triggered set of medical follow-up messages. And, while both these are going on, the user may be chatting with an emotional support AI assistant (e.g., sara) on demand which could choose to follow-up on the user's emotional well-being at periodic intervals should the patient not message it for a specified period of time.

Figure 6A:
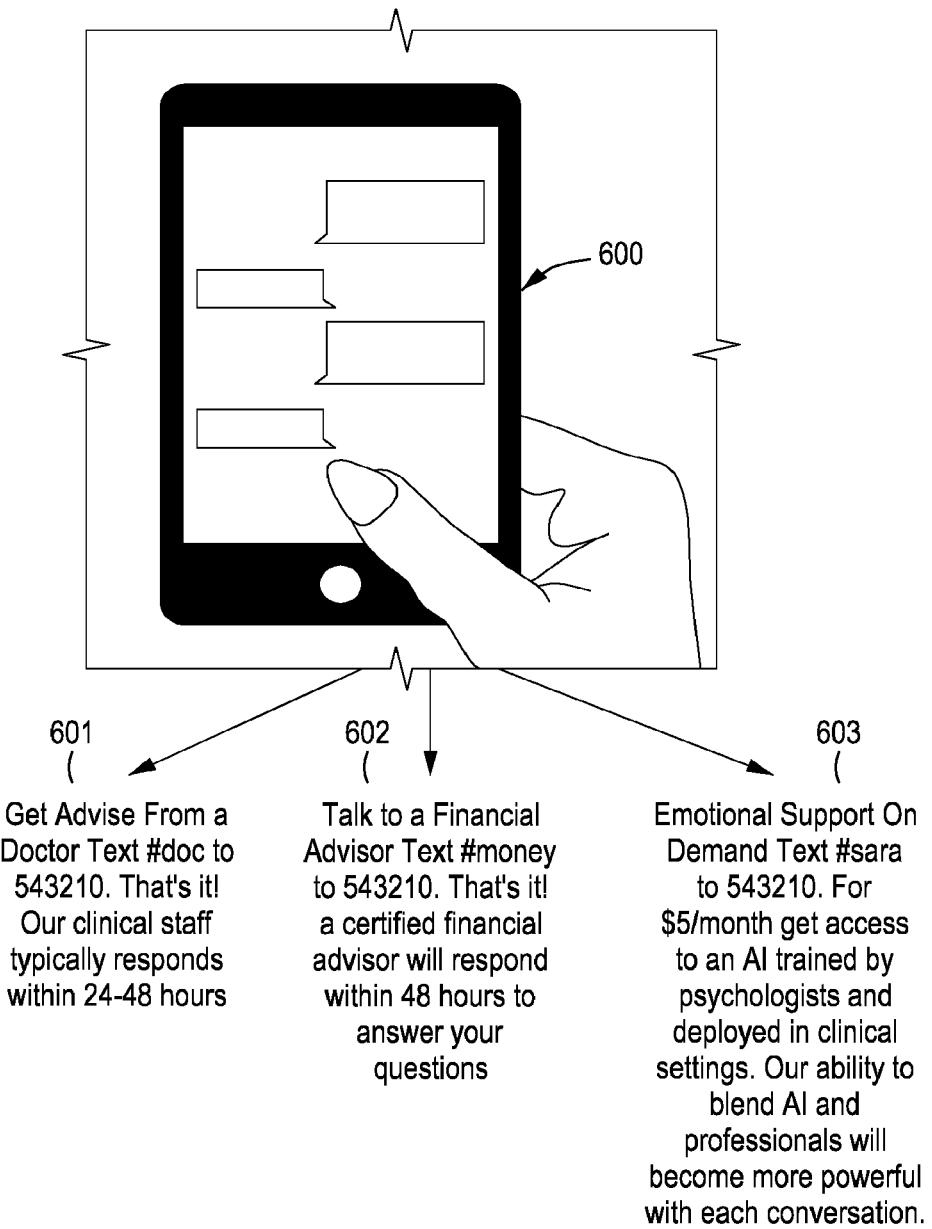
FIGS. 6A-B are graphic representations of example user interfaces showing example conversations between a user and an example system for AI assisted service provisioning and modification in connection with delivering message-based services, in accordance with one or more embodiments of the present disclosure.

FIG. 6A illustrates example conversations between a user and an example system for AI assisted service provisioning and modification in connection with delivering message-based services, in accordance with an embodiment of the present disclosure. As depicted herein, three example conversations 601, 602 and 603 are illustrated at the user's perspective. The first two conversations are engaged with professionals (e.g., a doctor and a financial advisor), and the third one conversation is, contingent on payment, a conversation with an chatbot or an AI assistant.

In conversation 601, a user at a messaging device 600 is requesting for advice from a doctor via the system. In some embodiments, the system can be implemented at, for example and without limitations, platform 106 of FIGS. 1A-B, cloud 108 of FIG. 1C, platform 206 of FIG. 2A, and platform 250 of FIG. 2B. To start the request, the user sends a text message of "#doc" to a short code of "543210" associated with the system. Subsequently, the user gets back a response of "That's it! Our clinician staff typically responds within 24-48 hours" from the system.

In conversation 602, the user at messaging device 600 is requesting for advice from a doctor via the system. To start the request, the user sends a text message of "#doc" to a short code of "543210" associated with the system. Subsequently, the user gets back a response of "That's it! Our clinician staff typically responds within 24-48 hours from the system.

In conversation 603, the user at messaging device 600 is requesting for on-demand emotional support via the system. To start the request, the user sends a text message of "#Sara" to the same short code of "543210" associated with the system. Subsequently, the user gets back a response from the system indicating that this type of service requires payment. Once the user makes the required payment, an example conversation exchanged between the user, Sara, and service professional are illustrated in Table 1.

In table 1 below, example dialog between a user that has engaged in a conversation initially conducted by a first bot (e.g., sara), then handed to a doctor, then another bot (e.g., survey bot), and finally the first bot (e.g., sara). It should be appreciated that a conversation can be handed from a bot/AI assistant to other bots/AI assistants, any professionals; from professionals to professionals; from professionals to any bots/AI assistants.

TABLE 1

| User | Sara (emotional support bot/AI assistant) | Notes on Handoffs |
|---|---|---|
| #sara | | |
| | Hello, I'm Sara! Think of me as a source of support, to reach out whenever you're feeling low, or when you just want to chat. While I am not a therapist, I am trained by psychologists and take your privacy seriously! | |

TABLE 1-continued

| User | Sara (emotional support bot/AI assistant) | Notes on Handoffs |
|---|---|---|
| | You can read more about the privacy policy here. http://bit.ly/2qTXihj. OK? | |
| It's ok | | |
| | I am eager to get to know you! What's your name? | |
| Chandra | | |
| | It's great to meet you Chandra. Let's get started. I'd like you to take a moment to think about how your week has been and how you're feeling. Tell me what comes to mind . . . | |
| I'm a little sad this week. Very busy too. | | |
| | Thanks so much for sharing that. Have you felt this way before? | |
| Sometimes | | |
| | Have you received support for this in the past? | |
| Occasionally | | |
| | That's good to know, Chandra. It helps me to get a sense of what you're going through. Would you like me to explain a bit more about what you can expect from our time together? | |
| No, that's ok. | | |
| | Alright, since I am available anytime you need, it is best to start with one emotion or topic to focus on first. What comes to mind? | |
| Anxiety | | |
| | Do you want to talk about feeling anxious, Chandra? | |
| Yes, a little | | |
| | That's fine. I assume you prefer to stay on topic. Alright, since I am available anytime you need, it is best to start with one emotion or topic to focus on first. What comes to mind? | |
| Anxiety | | |
| | I understand. I can offer some strategies to cope with this. Should we go through one together? | |
| Yes | | |
| | Sometimes we convince ourselves of things that are not really true. These types of things are not really true. These types of thoughts are called cognitive distortions and usually reinforce negative thinking patterns. Bringing awareness to your thought patterns can help reframe them in a more accurate and positive light. Allow me to provide a few examples, ok? | |
| That's ok | | |
| | As we continue, think about how these types of thoughts apply to you. It is important to understand your own thought patterns A common distortion is called "all-or-nothing" thinking. An example of this is when you fail once and you convince yourself that you will continue to fail at everything. Have you experienced something similar? | |
| I've never but not sure | | |
| | For example, a person with this mindset will think they are a complete failure if they ate a cookie while on a diet. Can you think of any instances where you have had thoughts like this? | |
| Can't at the moment | | |
| | Okay good. Chandra! Re-attribution is a great way to fight the | |

TABLE 1-continued

| User | Sara (emotional support bot/AI assistant) | Notes on Handoffs |
|---|---|---|
| | habit of assuming that everything is your fault. Try switching your focus on solving the problem instead of blaming yourself. Is that clear? | |
| Not clear | | |
| | For example, if a friend cancels dinner plans rather than blaming yourself, list other reasons why they might have cancelled. Perhaps they were feeling financial stress, social anxiety, etc. Does this make sense? | |
| Sort of but | | |
| | It's okay, Chandra. That's why we're going through these together. Being aware is the first step to combating these troublesome thoughts!<br>It is also important to pay attention to your mental filter. Do you find yourself dwelling on the negatives and ignoring the positives in your life? | |
| Now and then | | |
| | That's alright, Chandra. Focusing on the negative can be exhausting!<br>Switching your focus can be very useful. Every time you focus on something negative in your life, try to list a few positive things that you are grateful for! What is one thing you are grateful for right now? | |
| Being busy | | |
| | Alright, let's continue<br>I had a chat with a woman who repeatedly discredited her accomplishments. She insisted that she was only offered a job because the company was desperate rather than because she had earned it. Do you ever think like this? | |
| I do | | |
| | This type of thinking makes it hard to reward yourself. It can weigh you down, impacting your self-esteem and your relationships.<br>This impact to relationships also occurs when we jump to conclusions. Do you know what I mean? | |
| Not really | | |
| | Here is a specific example. Ben's crush hasn't talked to him in a few weeks so he assumes that she doesn't like him and he withdraws from her. Later, he finds out she was preoccupied with family issues. Can you think of a time when you have jumped to a conclusion that wasn't right? | |
| I'm really depressed. I don't know what to do. | I'm very sorry to hear that. Let me have someone else talk to you about that. | "really depressed" and the context about the user's anxiety triggers this message, and escalates it internally. |
| | Hi, this is Doc. Woodland. I'm a licensed counselor. Sara alerted me to talk to you. Would that be alright? | If it is escalated to a professional, the professional informs the user who he is and ask the user's permission to continue. |
| Sure | | |
| | Great. Can you tell me more about how you're feeling? | |
| I'm feeling . . . | (back and forth conversation continues)<br>Can I ask you take a short survey about how you're feeling? It's medically standard and It'll help me get you the help you need and deserve. | Professional is asking the user to go into a bot. |
| Sure | Great. I'll kick off the survey now. | Professional picks the bot and assigns it to the user. |
| | Hi Chandra. I have a few questions to ask. It'll just take a few minutes. | |

TABLE 1-continued

| User | Sara (emotional support bot/AI assistant) | Notes on Handoffs |
| --- | --- | --- |
| Ok | Over the past two weeks, have you found that you've had little interesting in doing things? Respond with 1 for Not at All, 2 for Several Days, 3 for More than Half the Days, or 4 for Every Day | |
| 3 | (bot conversation continues) | |
| | That's it! Thanks for answering. I'll pass the conversation back to Dr. Woodland Hi Chandra. This is Dr. Woodland again. I have some thoughts based on your responses. Would you like to go through them now? | Bot passes back to a professional. |
| Ok | | Professional is once again talking to a user. Decides that the situation is not an emergency. Recommends an appointment. |
| | Here's the link to book a face-to-face appointment with a psychologist. <link> Please book as soon as you can. | |
| Ok | In the meantime, would you like to talk to Sara again? | |
| Yes | Great. I'll hand you off. Please text #talk if you want to talk to me or one of my colleagues again. We're here to help! Goodbye. Hi Chandra! This is Sara. Would you like to talk about some techniques to manage stress? | Professional reactivates Sara, the bot. |

Figure 6B:
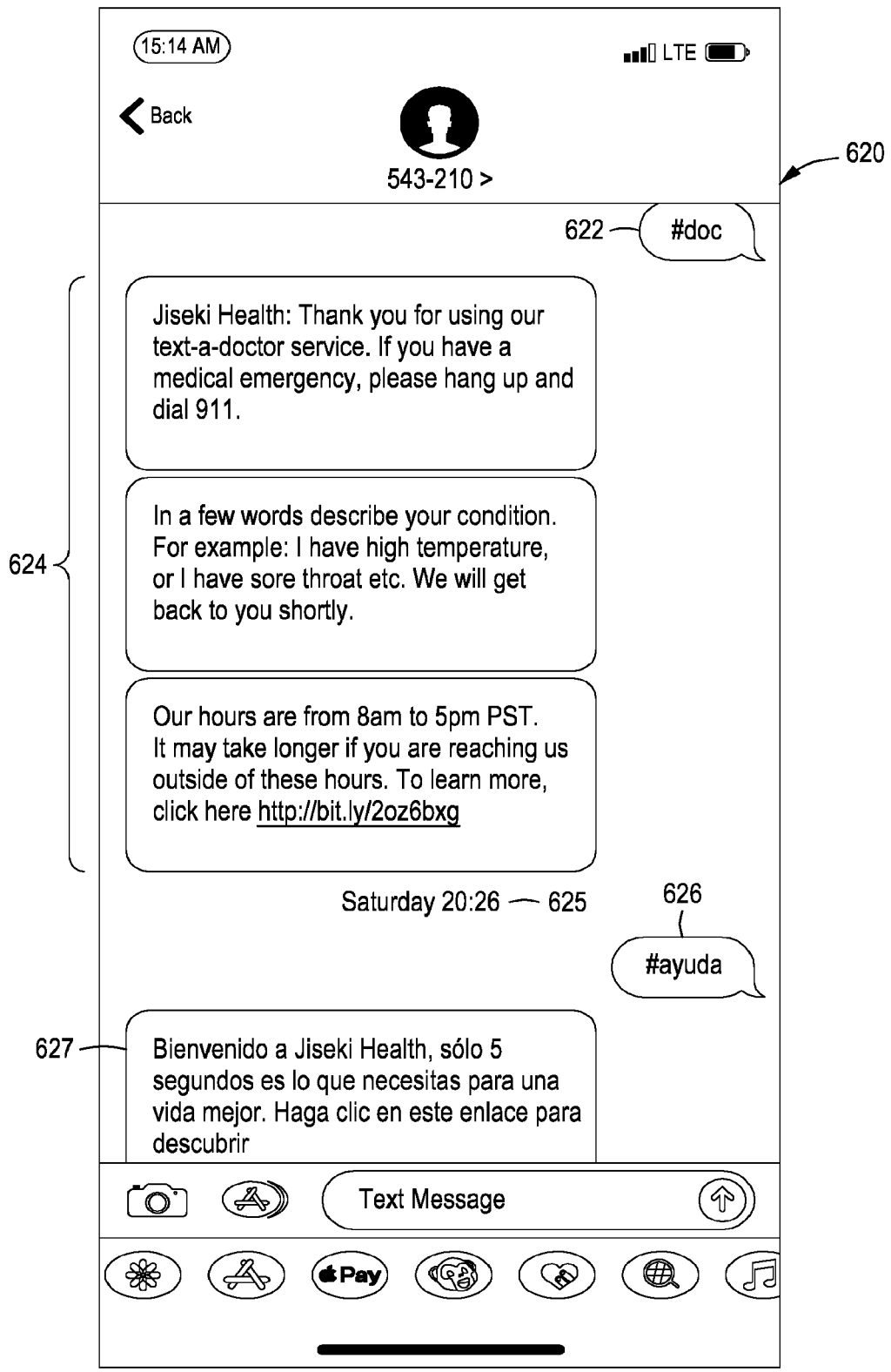

FIG. 6B illustrates a graphic representation of an example user interface showing another example conversations between a user and an example platform for AI assisted service provisioning and modification in connection with delivering message-based services. As shown herein, user interface 620 displays a message 622 (e.g., "#doc") to a short code 543-210. Subsequently, the platform responds with one or more messages 624 with a timestamp 625. In some embodiments, in one of the one or more messages 624, the platform provides the user with a link to travers to the web page guide of the platform. Next, the user texts a message 626 in a different language (e.g., #ayuda), and the platform responds with message 627 in the same different language as used in message 626.

Figure 7A:
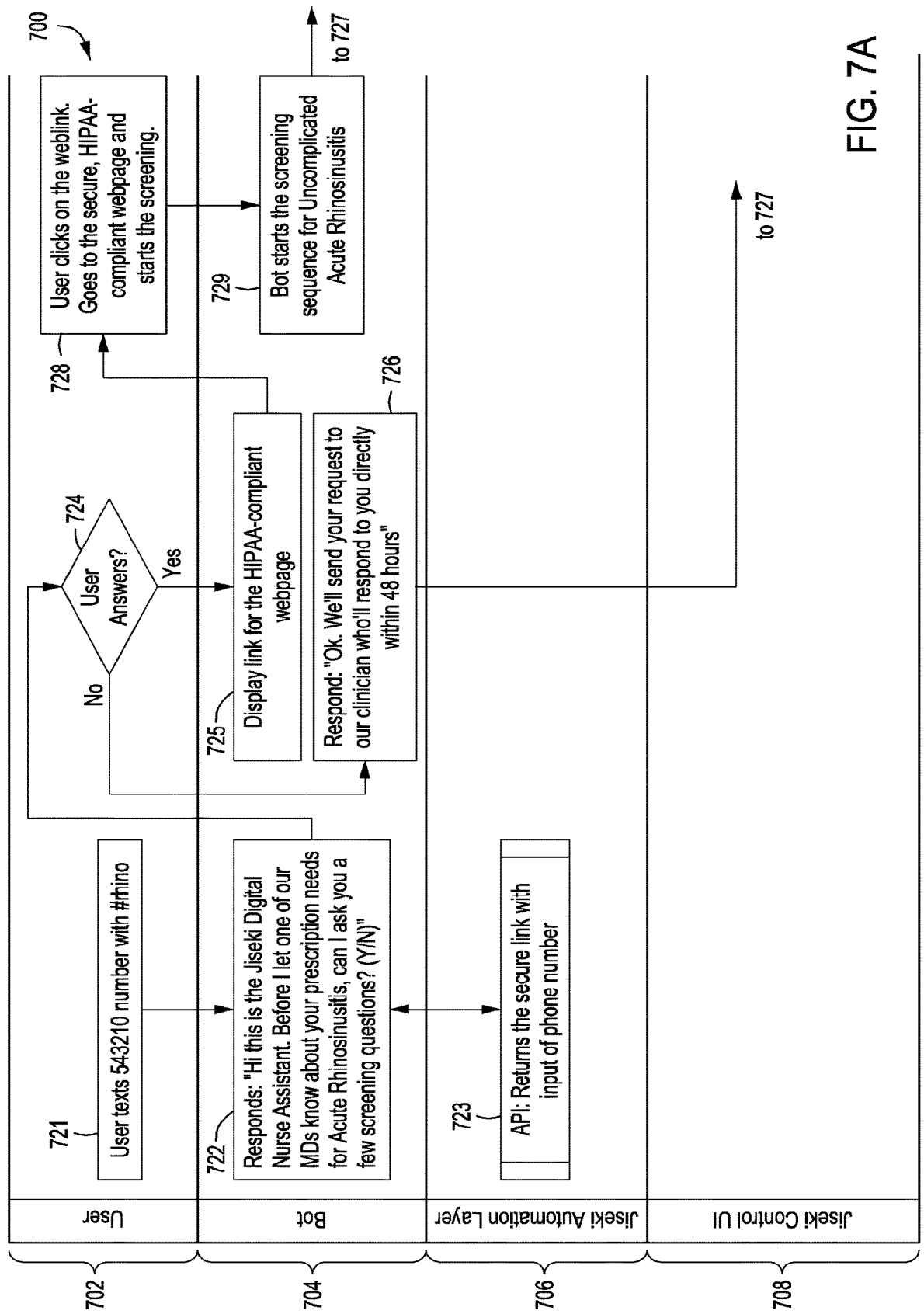
FIGS. 7A-B are a simplified flow diagram of an example workflow for AI assisted service provisioning and modification in connection with delivering message-based services, in accordance with one or more embodiments of the present disclosure.
Figure 7B:
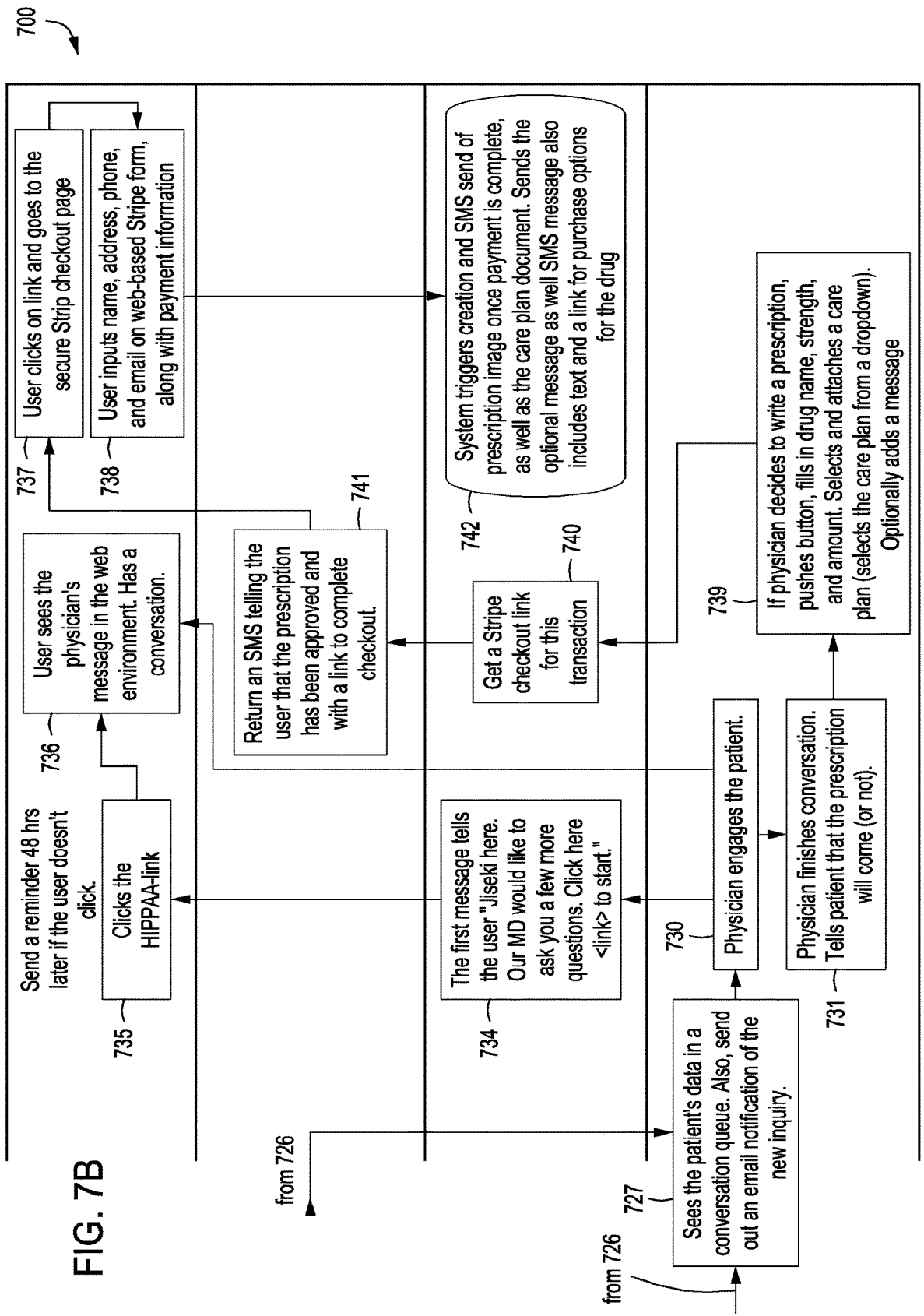

FIGS. 7A-B illustrate a simplified flow diagram of an example workflow for AI assisted service provisioning and modification for delivering message based service, in accordance with an embodiment of the present disclosure. In this example, the workflow of conversations originates from four domains: user 702, chatbot 704, Jiseki Administration 706, and Jiseki control UI (e.g., internal UI 214 of FIG. 2A).

In some embodiments, the platform is configured with privacy safeguards (e.g., HIPAA compliance safeguards) so that the platform can engage a user in a conversation about, for example, personal finance topics, diet, or general well-being, without forcing the user into a more secure environment as one of the privacy concerns (e.g., HIPAA) is raised. This is determined based on information gathered as the workflow interaction requires it, or a professional determines so. In some embodiments, mechanisms such as secure messaging, one-time access links are sent to users so that to migrate/move them from normal messaging platforms to special web-hosted, browser-accessed secure environments, which conform to more stringent healthcare requirements but take users away from the message platforms they're familiar with. In some embodiments, this is performed on need-only basis. For example, manual and automated conversations are allowed to be mixed flexibly, supporting moving the user from normal conversation to HIPAA-compliant clinical conversations (including web calling) and back again.

In some embodiments, input tokens may be connected to complicated flows leading to a mix of professional interventions and scripted services, such as illustrated in the flowchart of FIGS. 7A-B. As shown in FIGS. 7A-B, a protocol-driven assessment for the medical condition (e.g., rhinosinusitis) leads potentially to a prescription and the issuance of a care plan to the user based on physician discretion. The platform (e.g., platform 106 of FIGS. 1A-B, cloud 108 of FIG. 1C etc.) allows customization of these workflows to include messaging across channels, involve partner companies, and encompass simple and complex exchanges of information, service, and expertise. In FIGS. 7A-B, a Jiseki workflow with a particular prescription-delivery partner is shown herein. In general, the workflow includes, for example, multiple actors and entities, automated follow-ups, secure modes of communication when needed, and payment processing.

In more details, at 721, a user 702 sends a text of "#rhnio" to a short code of "543210" associated with the platform, which in turn is received and responded to by a chatbot 704. In this example, chatbot 704 replies to user 702 with a text message of "Hi this is the Jiseki Digital Nurse Assistant. Before I let one of our MDs know about your prescription needs for Acute Rhinosinusitis, can I ask you a few screening questions? (Y/N)." Upon receiving the message, user 702 may decide to rely with an answer of "yes" or "no" at 724. When user 702 answers with a "yes," at 725, chatbot 704 sends to user 702 a message including a link for the HIPAA-compliant webpage for conducting the survey. In some embodiments, chatbot 704 notifies Jiseki Administration 706 to generate a secure link with the input such as the use's phone number at 723. On the other hand, when user 702 answers with a "no," at 726, chatbot 704 sends another message of "OK. We'll send your request to our clinician who'll respond to you directly within 48 hours" to user 702.

Once presented with the link sent from chatbot 704, user 702 clicks on the secure link to go to the secure and HIPAA-compliant webpage, and starts the screening via the webpage at 728. Once user 702 is engaged in a screening session using the link sent by chatbot 704, chatbot 704 starts the screening sequence for user 702 at 729, if deciding that this is an uncomplicated case.

In either case of chatbot 704 conducting the screening or a clinician conducting the screening, at 727, a professional (e.g., a nurse) or an AI assistant at Jiseki control UI 708 sees user 702's data in a conversation queue, and subsequently sends out an email notification of the new inquiry to a physician. At 730, the physician (also at control UI 708) engages user 702 with respect to the requested care by having Jiseki Administration 706 end a first message to user 702, indicating that "Jiseki here, our MD would like to ask you a few more questions. Click here <link> to start" at 734. Upon receiving the first message, user 702 clicks on the link embedded therein at 735 to see the physician's message in the web environment and converse with the physician in the web environment at 736. In some embodiments, Jiseki Administration 706 also sends user 702 a reminder in case where user 702 does not respond to the first message sent at 734 after 48 hours.

Afterwards and at 731, the physician finishes the conversation with user 702, and informs user 702 that the prescription will come or not needed, depending on the physician's opinion based on the conversation. In the scenarios where the physician does decide to prescribe medications for user 702, at 739 and via control UI 708, the physician clicks on the "Rx" button (e.g., "Rx" button 457 of FIG. 4C) to fill information such as the drug name, strength, amount, and instructions. The physician can also select and attach a care plan (e.g., from a dropdown interface element of control UI 708), and/or adds a message.

Next at 740, Jiseki Administration 706 generates a payment link (e.g., a Stripe checkout link) for the prescription. At 741, chatbot 704 sends a message to user 702 that the prescription has been approved, and the message includes a link to complete a checkout. At 737, upon receiving the message sent from chatbot 704 at 741, user 702 clicks on the link and goes to the secure Stripe checkout page at 737, and in turn enters the information required for the check out, such as name, address, phone number, email address, payment information etc., on the web based Stripe checkout form at 738.

Finally at 742, Jiseki Administration 706 triggers the creation of an SMS message to send the image of the prescription once the payment is processed. In cases where the physician attaches a care plan or an optional message, Jiseki Administration 706 also sends to user 702 the care plan, and/or the optional message. In some embodiments, Jiseki Administration 706 also sends a message including a link of options to purchase the prescription.

FIG. 8 is a functional diagram illustrating an embodiment of a programmed computer system for AI assisted service provisioning and modification for delivering message-based services. As will be apparent, other computer system architectures and configurations can be used to display data. Computer system 800, which includes various subsystems as described below, includes at least one microprocessor subsystem (also referred to as a processor or a central processing unit (CPU)) 802. For example, processor 802 can be implemented by a single-chip processor or by multiple processors. In some embodiments, processor 802 is a general purpose digital processor that controls the operation of the computer system 800. Using instructions retrieved from memory 810, the processor 802 controls the reception and manipulation of input data, and the output and display of data on output devices (e.g., display 818). In some embodiments, processor 802 includes and/or is used to provide the launch of a client application based on a message.

Processor 802 is coupled bi-directionally with memory 810, which can include a first primary storage area, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 802. Also as is well known in the art, primary storage typically includes basic operating instructions, program code, data, and objects used by the processor 802 to perform its functions (e.g., programmed instructions). For example, memory 810 can include any suitable computer readable storage media, described below, depending on whether, for example, data access needs to be bi-directional or uni-directional. For example, processor 802 can also directly and very rapidly retrieve and store frequently needed data in a cache memory (not shown).

A removable mass storage device 812 provides additional data storage capacity for the computer system 800 and is coupled either bi-directionally (read/write) or uni-directionally (read only) to processor 802. For example, storage 812 can also include computer readable media such as magnetic tape, flash memory, PC-CARDS, portable mass storage devices, holographic storage devices, and other storage devices. A fixed mass storage 820 can also, for example, provide additional data storage capacity. The most common example of fixed mass storage 820 is a hard disk drive. Mass storage 812, 820 generally store additional programming instructions, data, and the like that typically are not in active use by the processor 802. It will be appreciated that the information retained within mass storages 812 and 820 can be incorporated, if needed, in standard fashion as part of memory 810 (e.g., RAM) as virtual memory.

In addition to providing processor 802 access to storage subsystems, bus 814 can also be used to provide access to other subsystems and devices. As shown, these can include a display 818, a network interface 816, a keyboard 804, and a pointing device 808, as well as an auxiliary input/output device interface, a sound card, speakers, and other subsystems as needed. For example, the pointing device 808 can be a mouse, stylus, track ball, or tablet, and is useful for interacting with a graphical user interface.

The network interface 816 allows processor 802 to be coupled to another computer, computer network, or telecommunications network using a network connection as shown. For example, through the network interface 816, the processor 802 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 802 can be used to connect the computer system 800 to an external network and transfer data according to standard protocols. For example, various process embodiments disclosed herein can be executed on processor 802, or can be performed across a network such as the Internet, intranet networks, or local area networks, in conjunction with a remote processor that shares a portion of the processing. Additional mass storage devices (not shown) can also be connected to processor 702 through network interface 816.

An auxiliary I/O device interface (not shown) can be used in conjunction with computer system 800. The auxiliary I/O device interface can include general and customized interfaces that allow the processor 802 to send and, more typically, receive data from other devices such as microphones, touch-sensitive displays, transducer card readers, tape readers, voice or handwriting recognizers, biometrics readers, cameras, portable mass storage devices, and other computers. Persons skilled in the art may clearly understand that, for the sake of descriptive convenience and streamlining, one may refer to the processes in the aforesaid method embodiments that correspond to specific work processes of the systems, devices, and units described above. They will not be discussed further here.

For a touch-sensitive display (also called "touch screen" or "touch display screen"), the display an include a graphical user interface (GUI). The user may interact with the GUI display via various operations such as touching with a finger, touching with a hand, and/or gesture. Via the human-computer interactions, various functionalities can be achieved including: creating a web page, drawing, text processing, editing an electronic document, playing games, video conferencing, messaging, sending/receiving emails, making phone calls, playing video, playing audio, on-line browsing, and the like.

In one typical configuration, the computation equipment comprises one or more processors (CPUs), input/output interfaces, network interfaces, and memory.

Memory may include such forms as volatile storage devices in computer-readable media, random access memory (RAM), and/or non-volatile memory, such as read-only memory (ROM) or flash memory (flash RAM). Memory is an example of a computer-readable medium.

Computer-readable media, including permanent and non-permanent and removable and non-removable media, may achieve information storage by any method or technology. Information can be computer-readable commands, data structures, program modules, or other data. Examples of computer storage media include but are not limited to phase-change memory (PRAM), static random access memory (SRAM), dynamic random access memory (DRAM), other types of random access memory (RAM), read-only memory (ROM), electrically erasable programmable read-only memory (EEPROM), flash memory or other memory technology, compact disk read-only memory (CD-ROM), digit multifunction disc (DVD) or other optical storage, magnetic cassettes, magnetic tape or magnetic disc storage, or other magnetic storage equipment or any other non-transmission media that can be used to store information that is accessible to computers. As defined in this document, computer-readable media does not include temporary computer-readable media, (transitory media), such as modulated data signals and carrier waves.

A person skilled in the art should understand that embodiments of the present application can be provided as methods, systems, or computer program products. Therefore, the present application can take the form of an entirely hardware embodiment, an entirely software embodiment, or an embodiment that combines software and hardware aspects. In addition, the present application can take the form of computer program products implemented on one or more computer-operable storage media (including but not limited to magnetic disk storage devices, CD-ROMs, and optical storage devices) containing computer operable program codes.

Examples

Illustrative examples of the technologies disclosed herein are provided below. An embodiment of the technologies may include any one or more, and any combination of, the examples described herein below.

Example 1 includes a method for AI-assisted service provisioning and modification for delivering message-based services, the method comprising receiving, by a computing system, an input sequence from a user in relation to a request for a service; classifying, by the computing system, the input sequence into a set of one or more elements, wherein an element of the set of one or more elements is associated with at least one of the following: a communication mode, a communication type, and a priority; associating, by the computing system, the user with a workflow based at least in part on the set of one or more elements; and interacting, by the computing system, with the user based at least in part on the workflow to deliver the service.

Example 2 includes the subject matter of Example 1, and further including modifying, by the computing system, the workflow based on interaction data in relation to the delivering of the service. Example 3 includes the subject matter of any of Example 1-2, and wherein the workflow is generated based at least in part on information pertaining to one or more best practices, and/or one or more guidelines related to the service. Example 4 includes the subject matter of any of Example 1-3, and wherein associating the user with the workflow is further based at least in part on at least one of the following: data associated with a user profile of the user, data related to the interacting with the user to deliver the service, and data related to interacting with the user to deliver another service. Example 5 includes the subject matter of any of Example 1-4, wherein the modified workflow is stored corresponding to the user. Example 6 includes the subject matter of any of Example 1-5, and wherein modifying the workflow comprises modifying the workflow based at least in part on an interaction with the user on session other than the current one.

Example 7 includes the subject matter of any of Example 1-6, and wherein modifying the workflow comprises modifying the workflow based at least in part on an interaction by the computing system with another user. Example 8 includes the subject matter of any of Example 1-7, and wherein the input sequence from the user comprise a token indicating a field of service. Example 9 includes the subject matter of any of Example 1-8, and wherein the token is a hashtag. Example 10 includes the subject matter of any of Example 1-9, and wherein the workflow is provisioned with a set of one or more workflow steps, a step of the set of one or more workflow steps being performed by a bot, a professional personnel, a professional, or a combination thereof. Example 11 includes the subject matter of any of Example 1-10, and wherein the session is a messaging based communication. Example 12 includes the subject matter of any of Example 1-11, and furthering including associating, by the computing system, a context guard to a portion of the session between the user and the computing system. Example 13 includes a computing system comprising a processor, and a memory having stored therein a plurality of instructions that when executed by the processor cause the computing system to perform the method of any of Examples 1-12. Example 14 includes one or more machine-readable storage media comprising a plurality of instructions stored thereon that in response to being executed cause a computing to perform the method of any of Examples 1-12.

Although the foregoing embodiments have been described in some detail for purposes of clarity of understanding, the invention is not limited to the details provided. There are many alternative ways of implementing the invention. The disclosed embodiments are illustrative and not restrictive.

Although the technologies described herein are primarily described with reference to the healthcare field, financial field, etc., it should be appreciated that, in other embodiments, the technologies can be employed in relation to other fields.

The embodiments of the present application are described with reference to flowcharts and/or block diagrams based on methods, terminal equipment (systems), and computer program products of the embodiments of the present application. Please note that each flowchart and/or block diagram within the flowcharts and/or block diagrams and combinations of flowcharts and/or block diagrams within the flowcharts and/or block diagrams can be realized by computer commands. These computer program commands can be provided to the processors of general-purpose computers, specialized computers, embedded processor devices, or other programmable data processing terminals to produce a machine. The commands executed by the processors of the computers or other programmable data processing terminal equipment consequently give rise to devices for implementing the functions specified in one or more processes in the flowcharts and/or one or more blocks in the block diagrams.

The methods or algorithmic steps described in light of the embodiments disclosed herein can be implemented using hardware, processor-executed software modules, or combinations of both. Software modules can be installed in random-access memory (RAM), memory, read-only memory (ROM), electrically programmable ROM, electrically erasable programmable ROM, registers, hard drives, removable disks, CD-ROM, or any other forms of storage media known in the technical field.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for AI-assisted service provisioning and modification for delivering message-based services, comprising:
   receiving an input sequence from a user in relation to a request for a service, the input sequence including one or more input items;
   processing the input sequence to determine a service type;
   associating a workflow with the request based on the service type and a profile of the user, the workflow including a set of one or more steps, a step of the set of one or more steps corresponding to a set of attributes including at least one of: a communication mode, a communication type, or a communication priority, the workflow being performed by at least one of: a chatbot, an AI assistant, or a service professional;
   modifying the workflow based on a new input sequence from the user using a workflow engine comprising at least one of: an AI model, a machine learning model, and a ruleset,
   wherein the workflow engine is configured to perform at least one action to workflows selected from a group of actions composed of: starting, pausing, resuming, switching, updating, and stopping one or more of the workflows; and
   interacting with the user based at least in part on the workflow to deliver the service.

2. The method of claim 1, wherein the modifying of the workflow further comprises modifying the workflow based at least in part on communication with another user.

3. The method of claim 1, wherein the profile of the user is updated based at least in part on previous communication with the user to deliver a service of the same service type, and/or communication with the user to deliver a service of a type other than the service type.

4. The method of claim 1, wherein the workflow is generated by a rule engine evaluating a ruleset corresponding to the service type.

5. The method of claim 4, wherein a rule of the ruleset corresponding to the service type is modified using an artificial intelligence model trained based at least in part on communication related to delivering services of the service type.

6. The method of claim 1, wherein the input sequence from the user comprises a token indicating a service type.

7. The method of claim 6, wherein the token is a hashtag.

8. The method of claim 1, wherein the modifying of the workflow further comprises modifying the workflow based at least in part on the profile of the user.

9. The method of claim 1, wherein one or both of the input sequence and the new input sequence comprise at least one of: textual data, symbolic data, audio data, video data, AR data, and VR data.

10. The method of claim 1, wherein the interacting with the user based at least in part on the workflow to deliver the service comprises messaging the user via at least one of: text communication, audio communication, video communication, AR communication, and VR communication.

11. The method of claim 1, wherein the modifying the workflow comprises modifying and managing the workflow based on a parameter associated with the service.

12. The method of claim 1, wherein the parameter comprises a time constraint.

13. The method of claim 1, wherein the workflow manager is configured to allow a human operator to perform at least one action selected from a group of actions to workflows composed of: start, pause, resume, switch, update, and stop the workflows.

14. The method of claim 1, wherein the modifying the workflow comprises cross-communications with a separate workflow via outputting to and taking input from the separate workflow.

15. The method of claim 14, wherein the cross-communications with the separate workflow comprise modifying at least one of: a prioritization factor, a timing factor, a number of message limit, message content for one or both of the workflow and the separate workflow.

16. The method of claim 1, further comprising at least one of: storing the workflow, configuring an input mode, channel management, instruction management, rule management, and capability management.

17. The method of claim 1, wherein the workflow engine is trained based at least in part on one or more of: historical communication with the user to deliver a service of the same service type, historical communication with the user to deliver a service of a type other than the service type, historical communication with another user to deliver a service of the same service type, historical communication with the another user to deliver a service of a type other than the service type, and/or third-party data relating to the same service type and/or a service of a type other than the service type, the third-party data including data supplied from at least one of: a data service company, a partner, a public entity, a government entity, and a client.

18. A method to establish a workflow engine, comprising:
    obtaining at least one of: historical data associated with historical interactions between a platform and a plurality of users, current data associated with ongoing interactions between the platform and the plurality of users, third-party data, priorities associated with issues, time constraints, data gathered via input from entities performing workflows;
    training the workflow engine to associate a workflow with an incoming request from a user;
    training the workflow engine to detect cross-communication triggers in workflows;
    training the workflow engine to modify workflows based at least in part on at least one of: an AI model, a machine learning model, and a ruleset; and
    executing the workflow engine to delivery services to the user.

19. The method of claim 18, wherein workflow engine is configured to start, pause, stop, and modify the workflow.

20. The method of claim 18, wherein workflow engine is configured to update a profile associated with the user.

21. A method for managing a plurality of workflow associated with a user, comprising:
    monitoring a first workflow associated with the user, the first workflow initiated in response to a first new input sequence from the user;
    monitoring a second workflow associated with the user, the second workflow initiated in response to a second new input sequence from the user;
    detecting an interaction between the first workflow and the second workflow; and
    modifying at least one of the first workflow and the second workflow based on the detected interaction, wherein the modification comprises modifying content delivered to the user by combining content generated in association with the first workflow and the content generated in association with the second workflow.

22. The method of claim 21, wherein the modifying at least one of the first workflow and the second workflow based on the detected interaction comprises:
    determining at least one of a priority, a timing, and a message limit associated with the interaction; and
    modifying at least one of the first workflow and the second workflow based on at least in part on at least one of the a priority, a timing, and a message limit.

23. The method of claim 21, wherein the modifying at least one of the first workflow and the second workflow based on the detected interaction comprises modifying a first number of messages generated in association with the first workflow and a second number of generated in association with the second workflow such that a sum of the first number and the second number does not exceed a preconfigured number.

* * * * *